(12) United States Patent
Funamizu et al.

(10) Patent No.: US 10,291,831 B2
(45) Date of Patent: May 14, 2019

(54) IMAGE PROCESSING APPARATUS, IMAGING APPARATUS, AND MACHINE-READABLE MEDIUM STORING A PROGRAM

(71) Applicant: NIKON CORPORATION, Tokyo (JP)

(72) Inventors: Wataru Funamizu, Yokohama (JP); Hiroshi Ohki, Yokohama (JP); Shigeru Aoki, Yokohama (JP); Naoki Ohkouchi, Tokyo (JP); Toru Takagi, Fujisawa (JP); Yojiro Tezuka, Yokohama (JP); Sota Nakanishi, Kawasaki (JP)

(73) Assignee: NIKON CORPORATION, Tokyo (JP)

( * ) Notice: Subject to any disclaimer, the term of this patent is extended or adjusted under 35 U.S.C. 154(b) by 19 days.

(21) Appl. No.: 15/717,048

(22) Filed: Sep. 27, 2017

(65) Prior Publication Data

US 2018/0020143 A1 Jan. 18, 2018

Related U.S. Application Data

(63) Continuation of application No. PCT/JP2016/060384, filed on Mar. 30, 2016.

(30) Foreign Application Priority Data

Mar. 31, 2015 (JP) .................................. 2015-073351
May 29, 2015 (JP) .................................. 2015-110125

(51) Int. Cl.
*H04N 5/225* (2006.01)
*G06T 1/00* (2006.01)
(Continued)

(52) U.S. Cl.
CPC ....... *H04N 5/2256* (2013.01); *A61B 1/00009* (2013.01); *A61B 1/04* (2013.01);
(Continued)

(58) Field of Classification Search
CPC ...... H04N 1/484; H04N 5/225; H04N 5/2256; H04N 5/232; H04N 5/2351; H04N 5/2354;
(Continued)

(56) References Cited

U.S. PATENT DOCUMENTS

| 5,667,474 A | 9/1997 | Nishimura |
| 5,908,294 A | 6/1999 | Schick et al. |

(Continued)

FOREIGN PATENT DOCUMENTS

| JP | H07-246185 A | 9/1995 |
| JP | 2010-172638 A | 8/2010 |
| JP | 4826355 B2 | 11/2011 |

OTHER PUBLICATIONS

Jun. 28, 2016 International Search Report issued in International Patent Application No. PCT/JP2016/060384.

(Continued)

*Primary Examiner* — Lin Ye
*Assistant Examiner* — Chriss S Yoder, III
(74) *Attorney, Agent, or Firm* — Oliff PLC

(57) ABSTRACT

Provided is an image processing apparatus including as image acquiring section that acquires a plurality of images obtained by imaging, at different times, a subject irradiated with lights intensity-modulated with a plurality of modulation frequencies or modulation frequency bands; and a demodulating section that demodulates pixel values of the plurality of images with a plurality of demodulation frequencies or demodulation frequency bands based on the plurality of modulation frequencies or modulation frequency bands, for each pixel, thereby generating a plurality of pieces of pixel information indicating subject light amounts from the subject caused by each of the lights intensity- (Continued)

modulated with the plurality of modulation frequencies or modulation frequency bands, for each pixel.

28 Claims, 8 Drawing Sheets

(51) Int. Cl.
| | |
|---|---|
| *H04N 5/232* | (2006.01) |
| *H04N 5/238* | (2006.01) |
| *H04N 9/07* | (2006.01) |
| *A61B 1/00* | (2006.01) |
| *A61B 1/04* | (2006.01) |
| *A61B 1/06* | (2006.01) |
| *A61B 1/313* | (2006.01) |
| *H04N 5/235* | (2006.01) |
| *H04N 5/341* | (2011.01) |
| *H04N 5/351* | (2011.01) |
| *H04N 9/04* | (2006.01) |
| *H04N 1/48* | (2006.01) |

(52) U.S. Cl.
CPC .......... *A61B 1/0638* (2013.01); *A61B 1/0684* (2013.01); *A61B 1/3132* (2013.01); *G06T 1/00* (2013.01); *H04N 1/484* (2013.01); *H04N 5/225* (2013.01); *H04N 5/232* (2013.01); *H04N 5/238* (2013.01); *H04N 5/2351* (2013.01); *H04N 5/2354* (2013.01); *H04N 5/341* (2013.01); *H04N 5/351* (2013.01); *H04N 9/04521* (2018.08); *H04N 9/07* (2013.01); *H04N 2209/044* (2013.01)

(58) Field of Classification Search
CPC ........ H04N 5/238; H04N 5/341; H04N 5/351; H04N 9/04521; H04N 9/07; H04N 2209/044; G06K 9/2027; G06K 9/2036; G06K 9/4661; G06T 1/00; G03B 15/0457; A61B 1/04; A61B 1/06; A61B 1/063; A61B 1/0638; A61B 1/0646; A61B 1/0651; A61B 1/0653; A61B 1/0684; A61B 1/3132; A61B 1/00009
See application file for complete search history.

(56) References Cited

U.S. PATENT DOCUMENTS

| | | | |
|---|---|---|---|
| 7,652,559 B2 | 1/2010 | Chinomi et al. | |
| 8,928,802 B2* | 1/2015 | Peuser | .................. G03B 15/03 |
| | | | 348/265 |
| 2014/0160318 A1* | 6/2014 | Blanquart | .............. A61B 1/045 |
| | | | 348/234 |

OTHER PUBLICATIONS

Jan. 23, 2019 Search Report issued in European Patent Application No. 16772654.0.

\* cited by examiner

IMAGE PROCESSING APPARATUS, IMAGING APPARATUS, AND MACHINE-READABLE MEDIUM STORING A PROGRAM

The contents of the following patent applications are incorporated herein by reference:
Japanese Patent Application No. 2015-073351 filed on Mar. 31, 2015,
Japanese Patent Application No. 2015-110125 filed on May 29, 2015, and
International Patent Application PCT/JP2016/060384 filed on Mar. 30, 2016.

BACKGROUND

1. Technical Field

The present invention relates to an image processing apparatus, an imaging apparatus, and a machine-readable medium storing thereon a program.

2. Related Art

Technology is known for disassembling a time-fluctuating component of a video image for each frequency region, based on a captured video image, as shown in Patent Document 1, for example. Patent Document 1: Japanese Patent No. 4826355

If a subject is imaged with lights having different characteristics, the time resolution is worsened when radiating each light according to time division. For example, the time resolution worsened, as a result of imaging a subject using lights with a plurality of wavelength regions, when using an imaging method that includes radiating light with each wavelength region according to time division and receiving the light with each wavelength region in time division.

SUMMARY

According to a first aspect of the present invention, provided is an image processing apparatus comprising an image acquiring section that acquires a plurality of images obtained by imaging, at different times, a subject irradiated with lights intensity-modulated with a plurality of modulation frequencies or modulation frequency bands; and a demodulating section that demodulates pixel values of the plurality of images with a plurality of demodulation frequencies or demodulation frequency bands based on the plurality of modulation frequencies or modulation frequency bands, for each pixel, thereby generating a plurality of pieces of pixel information indicating subject light amounts from the subject caused by each of the lights intensity-modulated with the plurality of modulation frequencies or modulation frequency bands, for each pixel.

According to a second aspect of the present invention, provided is an imaging apparatus comprising the image processing apparatus described above and an image sensor that captures the plurality of images.

According to a third aspect of the present invention, provided is an imaging apparatus comprising a light source that emits lights intensity-modulated with a plurality of modulation frequencies or modulation frequency bands; an image sensor that images a subject irradiated by the lights; and an output section that outputs a plurality of images of the subject captured at different times by the image sensor, in association with information indicating the plurality of modulation frequencies or modulation frequency bands, to an image processing apparatus that, for each pixel, performs demodulation with a plurality of demodulation frequencies or demodulation frequency bands based on the plurality of modulation frequencies or modulation frequency bands.

According to a fourth aspect of the present invention, provided is a machine-readable medium storing thereon a program that causes a computer to acquire a plurality of images obtained by imaging a subject irradiated with lights intensity-modulated with a plurality of modulation frequencies or modulation frequency bands differing from each other; and demodulate pixel values of the plurality of images with a plurality of demodulation frequencies or demodulation frequency bands based on the plurality of modulation frequencies or modulation frequency bands, for each pixel, thereby generating a plurality of pieces of pixel information indicating subject light amounts from the subject caused by each of the lights intensity-modulated with the plurality of modulation frequencies or modulation, frequency bands, for each pixel.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
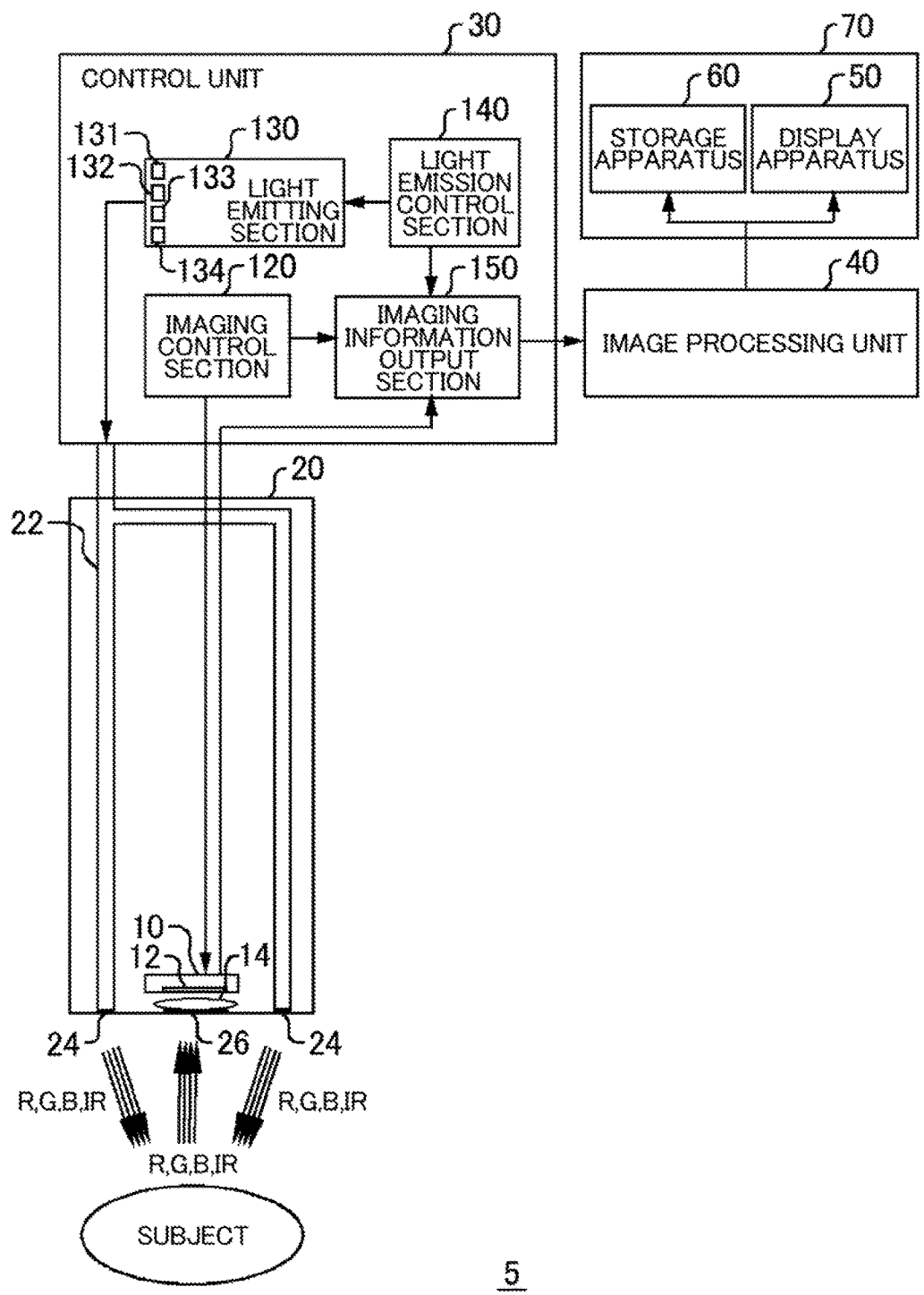
FIG. 1 schematically shows as imaging system 5 according to a present embodiment, together with a subject.

FIG. 1 schematically shows an imaging system 5 according to a present embodiment, together with a subject. The imaging system 5 is used as a laparoscopic imaging system. The subject is a living organism such as a human body, for example.

The imaging system 5 includes a scope section 20, a control unit 30, an image processing unit 40, and an output apparatus 70. The output apparatus 70 includes a display apparatus 50 and a storage apparatus 60. The display apparatus 50 is a display or the like for displaying a monitor image or the like of the inside of a body undergoing laparoscopic surgery. The storage apparatus 60 is a non-volatile storage medium such as a hard disk, for example, and stores the images or the like of the inside of the body undergoing laparoscopic surgery. The output apparatus 70 may include a communication apparatus or the like that transmits the images or the like of the inside of the body undergoing laparoscopic surgery to another apparatus via an external network.

The scope section 20 includes an imaging element 10, an objective lens 34, and a light guide 22. The imaging element 10 is provided near a tip portion of the scope section 20. The scope section 20 includes a light emission opening 24 and a light input opening 26 at the tip portion of the scope section 20. The light guide 22 is optically connected to the light emission opening 24. The light input opening 26 is provided opposite the objective lens 14, which is provided to an imaging section 12 of the imaging element 10.

The light emitting section 130 emits light having different characteristics from each other. These light characteristics include the wavelength region associated with the light, the modulation frequency with which the light intensity is modulated, and the like. The light emitting section 130 includes a light source 131, a light source 132, a light source 133, and a light source 134. The light source 131, the light source 132, the light source 133, and the light source 134 may be LED light sources. In the present embodiment, the light source 131, the light source 132, the light source 133, and the light source 134 each emit light with a different characteristic. Specifically, the light source 131 emits light associated with a red wavelength region. The light source 132 emits light associated with a green wavelength region. The light source 133 emits light associated with a blue wavelength region. The light source 134 emits light associated with an infrared wavelength region. Red, green, and blue are each an example of one color component in a wavelength region of visible light. Furthermore, the light associated with the red wavelength region is sometimes referred to as R light. Similarly, the light associated with the green wavelength region is sometimes referred to as G light, the light associated with the blue wavelength region is sometimes referred to as B light, and the light associated with the infrared wavelength region is sometimes referred to as IR light.

The light emission control section 140 causes the light source 131 to emit R light that is intensity-modulated with a modulation frequency f1, by controlling the drive of the light source 131. Furthermore, the light emission control section 140 causes the light source 132 to emit G light that is intensity-modulated with a modulation frequency f2, by controlling the drive of the light source 132. The light emission control section 140 causes the light source 133 to emit B light that is intensity-modulated with a modulation frequency B, by controlling the drive of the light source 133. The light emission control section 140 causes the light source 134 to emit IR light that is intensity-modulated with a modulation frequency f4, by controlling the drive of the light source 134. The light emission control section 140 emits light obtained by overlapping (superimposing) the R light, G light B light, and IR light by controlling the drive of each light source. As one example, f1=100 Hz, f2=200 Hz, f3=400 Hz, and f4=50 Hz. In this way, the light emission control section 140, the light emitting section 130, and the light guide 22 function as a light emitting section that emits lights with a plurality of wavelength regions that are intensity-modulated with different modulation frequencies from each other. The light emission control section 140, the light emitting section 130, and the light guide 22 are one example of a light emitting section that emits lights that are intensity-modulated with different modulation frequencies from each other, information indicating the values of f1, f2, f3, and f4, which are the modulation frequencies, is supplied to the imaging information output section 150 from the light emission control section 140.

The R light from the light source 131 modulated with the modulation frequency f1, the G light from the light source 132 modulated with the modulation frequency f2, the B light from the light source 133 modulated with the modulation frequency f3, and the IR light from the light source 134 modulated with the modulation frequency f4 are superimposed on each other and supplied to the light guide 22. The light guide 22 is formed of optical fiber, for example. The light guide 22 guides the R light, the G light, the B light, and the IR light supplied from the light emitting section 130 to the light emission opening 24. The light that reaches the light emission opening 24 via the light guide 22 is emitted from the light emission opening 24 as emission light, which includes the R light, the G light, the B light, and the IR light as component lights. In this way, the R light, the G light, the B light, and the IR light from the light emitting section 130 are multiplexed and emitted from the light emission opening 24.

The imaging element 10 is formed including a MOS image sensor. The imaging section 12 is formed by an imaging region in which a plurality of pixel elements of a plurality of photodiodes or the like are arranged two-dimensionally in the imaging element. The imaging element 10 does not include a wavelength filter that separates the light from the subject into lights with a plurality of wavelength components. For example, the imaging element 10 does not include a color filter in which filters that selectively pass lights with different wavelength regions from each other and are arranged in a Bayer arrangement or the like, for example, are arranged two-dimensionally to correspond one-to-one with the plurality of pixel elements. Accordingly, each pixel element of the imaging section 12 receives the subject light from the subject, caused by the lights with the plurality of wavelength regions, at the same time. In this way, the wavelength region of the light that can be incident to each pixel element of the imaging section 12 is substantially the same for each pixel element.

The imaging section 12 images the subject by receiving the subject light, which is the light from the subject. Specifically, the imaging section 12 receives the subject light that includes the light returned from the subject as a result of being irradiated with the R light, the G light, the B light, and the IR light. The subject light includes R light that is emitted from the light emission opening 24 and reflected or scattered by the subject, G light that is emitted from the light emission opening 24 and reflected or scattered by the subject, B light that is emitted from the light emission opening 24 and reflected or scattered by the subject, and IR light that is emitted from the light emission, opening 24 and reflected or scattered by the subject.

The imaging control section 120 controls the imaging element 10 to cause the imaging section 12 to perform imaging with a frequency that is higher than each of the modulation frequency f1, the modulation frequency f2, the modulation frequency f3, and the modulation frequency f4, thereby causing the imaging section 12 to capture a plurality of images. For example, the imaging control section 120 causes the imaging section 12 to perform imaging at 800 Hz. In this way, the imaging control section 120 causes the imaging section 12 to image the subject, which is irradiated by the lights that have the plurality of wave-length regions and are intensity-modulated by the modulation frequencies f1, f2, f3, and f4 that are different from each other, with a higher frequency than each of these modulation frequencies.

As described further below, the imaging control section 120 may cause the imaging section 12 to perform imaging a plurality of times while changing the phase, with a frequency that is lower than at least one of the modulation frequency f1, the modulation frequency f2, the modulation frequency f3, and the modulation frequency f4.

The imaging information output section 150 acquires image signals of the plurality of images captured at different times by the imaging element 10, and outputs the image signals acquired from the imaging element 10 as image data to the image processing unit 40. The imaging information output section 150 outputs the image signals acquired from the imaging element 10 to the image processing unit 140, in association with the modulation frequency information supplied from the light emission control section 140. In this way, the imaging information output section 150 outputs a plurality of images, which are captured by the imaging section 12, of the subject irradiated with the lights having the plurality of wavelength regions, in association with the information indicating the modulation frequencies f1, f2, f3, and f4. In this way, the plurality of images captured by the imaging section 12 are output to the image processing unit 40 in association with the information indicating the modulation frequencies f1, f2, f3, and f4.

The image processing unit 40 demodulates the image signals acquired from the imaging information output section 150 based on the modulation frequency information, thereby generating various images. For example, the image processing unit 40 generates image data for display, and displays an image in the display apparatus 50 based on the generated image data. Furthermore, the image processing unit 40 generates image data for storage, and stores the generated image data in the storage apparatus 60.

Figure 2:
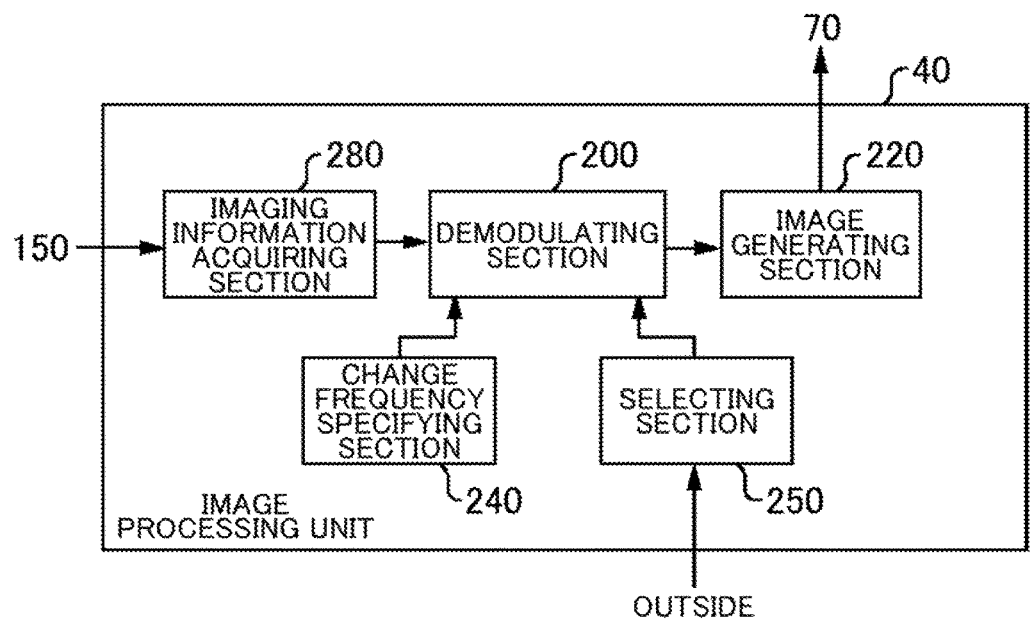
FIG. 2 is a block diagram showing the functional configuration of the image processing unit 40.

FIG. 2 is a block diagram showing the functional configuration of the image processing unit 40. The image processing unit 40 includes an imaging information acquiring section 280, a demodulating section 200, an image generating section 220, a change frequency specifying section 240, and a selecting section 250.

The imaging information acquiring section 280 acquires imaging information data acquired from the imaging information output section 150. The imaging information data includes a plurality of images of the subject irradiated by the R light intensity-modulated with the modulation frequency f1, the G light intensity-modulated with the modulation frequency f2, the B light intensity-modulated with the modulation frequency f3, and the IR light intensity-modulated with the modulation frequency f4. These images are images obtained by imaging the subject, which is irradiated by the lights having the plurality of wavelength regions intensity-modulated with the modulation frequencies f1, f2, f3, and f4 that are different from each other, with a frequency higher than any of the modulation frequencies f1, f2, f3, and f4.

Here, red is one example of a first color component associated with the visible region. Green is one example of a second color component associated with the visible region. The blue wavelength region is one example of a third color component associated with the visible region. The infrared wavelength region is one example of a wavelength region outside of the visible region. In other words, the imaging information acquiring section 280 acquires a plurality of images of the subject irradiated with the R light intensity-modulated with the modulation frequency f1, the G light intensity-modulated with the modulation frequency f2, and B light intensity-modulated with the modulation frequency f3.

The demodulating section 200 demodulates the pixel values of the plurality of images lot each pixel with a plurality of demodulation frequencies based on she plurality of modulation frequencies, thereby generating a plurality of pieces of pixel information indicating amounts of subject light from the subject caused by each of the lights intensity-modulated with the plurality of modulation frequencies, for each pixel. The pixel information generated by the demodulating section 200 has a scope that includes not only the actual values of subject light amounts for each pixel, but also values equivalent to the subject light amounts for each pixel. In the present embodiment, the demodulating section 200 demodulates the pixel values of the plurality of images with the plurality of demodulation frequencies based on the plurality of modulation frequencies, for each pixel, thereby generating a plurality of pieces of pixel information indicating the amounts of subject light from the subject caused by each of the lights having the plurality of wavelength regions, for each pixel. Specifically, the demodulating section 200 demodulates the pixel values of the plurality of images with a demodulation frequency based on the modulation frequency f1. For each pixel, thereby generating a plurality of pieces of pixel information indicating the amounts of subject light from the subject caused by the R light, for each pixel. Furthermore, the demodulating section 200 demodulates the pixel values of the plurality of images with a demodulation frequency based on the modulation frequency f2, for each pixel, thereby generating a plurality of pieces of pixel information indicating the amounts of subject light from the subject caused by the G light, for each pixel. The demodulating section 200 demodulates the pixel values of the plurality of images with a demodulation, frequency based on the modulation frequency f3, for each pixel, thereby generating a plurality of pieces of pixel information indicating the amounts of subject light from the subject caused by the B light, for each pixel. The demodulating section 200 demodulates the pixel values of the plurality of images with a demodulation frequency based on the modulation frequency f4, for each pixel, thereby generating a plurality of pieces of pixel information indicating the amounts of subject light from the subject caused by the IR light, for each pixel. Specifically, the demodulating section 200 demodulates the pixel values of the plurality of images with the modulation frequency f1, the modulation frequency f2, the modulation frequency f3, and the modulation frequency f4 for each pixel. In other words, the demodulation frequencies match the modulation frequencies. In this way, the demodulating section 200 demodulates the pixel values of the plurality of images with the plurality of modulation frequencies, for each pixel.

More specifically, the demodulating section 200 demodulates the pixel values of the plurality of images for each pixel with the modulation frequency f1, thereby generating the red pixel information for each pixel. Furthermore, fee demodulating section 200 demodulates the pixel values of the plurality of images for each pixel, with the modulation frequency f2, thereby generating the green pixel information for each pixel. The demodulating section 200 demodulates the pixel values of the plurality of images for each pixel with the modulation frequency f3, thereby generating the blue pixel information for each pixel. The demodulating section 200 demonstrates the pixel values of the plurality of images for each pixel with the modulation frequency f4, thereby generating the infrared pixel information for each pixel. In this way, the demodulating section 200 demodulates the pixel values of the plurality of images for each pixel with the plurality of modulation frequencies, thereby generating the plurality of pieces of pixel information for each pixel. It should be noted that, before performing the demodulation described above, the demodulating section 200 may perform pre-processing (a correction process) such as noise removal to compare each pixel to nearby pixels and remove noise. Furthermore, a correcting section may be provided between the imaging information acquiring section 280 and the demodulating section 200, and this correcting section may perform the pre-processing.

The image generating section 220 generates images caused by light from the subject resulting front each of the lights intensity-modulated with the plurality of modulation frequencies, based on the plurality of pieces of pixel information for each pixel generated by the demodulating section 200. In the present embodiment, the image generating section 220 generates the images caused by the light from the subject resulting from each of the lights having the plurality of wavelength regions, based on the plurality of pieces of pixel information for each pixel generated fry the demodulating section 200. Specifically, the image generating section 220 may generate a visible light image based on the red pixel information, the green pixel information, and the blue pixel information. Furthermore, the image generating section 220 may generate an infrared light image based on the infrared pixel information. The image generating section 220 may generate an image obtained by superimposing the infrared light image on the visible light image. The images generated by the image generating section 220 are output to the output apparatus 70. Furthermore, the image generating section 220 may separate the red pixel information, the green pixel information, the blue pixel information, and the infrared pixel information from the pixel information of each pixel element obtained when the imaging section 12 performed imaging, thereby generating the image resulting from background light that is not light from the light source 133. For example, the image generating section 220 may subtract the total value of the red pixel information, the green pixel information, the blue pixel information, and the infrared pixel information corresponding to each pixel element from the value obtained by performing time integration of the pixel information of each pixel element of the imaging section 12 according to a time based on the respective modulation frequencies, thereby generating the pixel information of the image caused by background light. Here, the time used for the time integration may be a period corresponding to the lowest frequency among the modulation frequencies f1, f2, f3, and f4.

The change frequency specifying section 240 performs a frequency analysis on the pixel information obtained by the demodulating section 200 performing demodulation with at least one modulation frequency among the plurality of modulation frequencies, thereby specifying the frequency fv of the change over time of the subject. The change over time of the subject is movement of the subject. The movement of the subject is a change over time of the position of the entire subject or a portion of the subject. The demodulating section 200 further demodulates the pixel values of the plurality of images with a frequency that is the sum of the modulation frequency f1 and the frequency fv, thereby generating pixel information representing the change over time of the subject. The demodulating section 200 further demodulates the pixel values of the plurality of images with a frequency that is the sum of the modulation frequency f2 and the frequency fv, thereby generating pixel information representing the change over time of the subject. The demodulating section 200 further demodulates the pixel values of the plurality of images with a frequency that is the sum of the modulation frequency f3 and the frequency fv, thereby generating pixel information representing the change over time of the subject. The demodulating section 200 further demodulates the pixel values of the plurality of images with a frequency that is the sum of the modulation frequency f4 and the frequency fv, thereby generating pixel information representing the change over time of the subject. In this way, the demodulating section 200 demodulates the pixel values of the plurality of images with frequencies that are each the sum of at least one modulation frequency among the plurality of modulation frequencies and the frequency of the change over time of the subject specified by the change frequency specifying section 240, thereby generating the pixel information representing the change over time of the subject. It should be noted that the demodulating section 200 may demodulate the pixel values of the plurality of images with frequencies that are each the difference between at least one modulation frequency among the plurality of modulation frequencies and the frequency of the change over time of the subject specified by the change frequency specifying section 240, thereby generating the pixel information representing the change over time of the subject. In this way, the demodulating section 200 may demodulate the pixel values of the plurality of images with frequencies that are each at least one of the difference between and the sum of at least one modulation frequency among the plurality of modulation frequencies and the frequency of the change over time of the subject specified by the change frequency specifying section 240, thereby generating the pixel information representing the change over time of the subject.

The demodulating section 200 may demodulate the pixel values of the plurality of images with frequencies that are each at least one of the sum of and the difference between at least one modulation frequency among the plurality of modulation frequencies and the frequency of the change over time of a plurality of groups each formed from a plurality of pixels, thereby generating a plurality of pieces of pixel information representing the change over time of the subject. For example, the change frequency specifying section 240 may perform a frequency analysis on the pixel information obtained by the demodulating section 200 performing demodulation with at least one modulation frequency among the plurality of modulation frequencies, for each of the plurality of groups formed from the plurality of pixels, thereby specifying the frequency fv of the change over time of the subject. The demodulating section 200 may perform demodulation with a frequency that is at least one of the sum of and the difference between at least one modulation frequency among the plurality of modulation frequencies and the frequency fv specified for each of the plurality of groups of pixels by the change frequency specifying section 240, thereby generating the pixel information representing the change over time of the subject for each of the plurality of groups of the pixels. As an example, a group formed from a plurality of pixels indicates a region showing the subject or a portion, of the subject within the image, and a plurality of the groups indicates that there are a plurality of such regions existing in the images.

The image generating section 220 may generate a change image that represents the change of the subject, based on the pixel information representing the change over time of the subject. The image generating section 220 may generate the image obtained by superimposing the change image on the visible light image described above. The image including the information of the change image generated by the image generating section 220 is output to the output apparatus 70.

If a change frequency of the subject is specified the demodulating section 200 may perform demodulation with a frequency that is the sum of at least one modulation frequency among the plurality of modulation frequencies and tire specified change frequency, without performing a frequency analysis on the image that has been demodulated with the modulation frequency. In this way, the demodulating section 200 generates the pixel signals representing the change over time of the subject by demodulating the pixel signals of the plurality of images with a frequency that is the sum of at least one modulation frequency among the plurality of modulation frequencies and a predetermined change frequency representing the frequency of the change over time of the subject. It should be noted that demodulating section 200 may generate the pixel signals representing the change over time of the subject by demodulating the pixel signals of the plurality of images with a frequency that is the difference between at least one modulation frequency among the plurality of modulation frequencies and a predetermined change frequency representing the frequency of the change over time of the subject. In this way, the demodulating section 200 may generate the pixel signals representing the change over time of the subject by demodulating the pixel signals of the plurality of images with a frequency that is at least one of the sum of and the difference between at least one modulation frequency among the plurality of modulation frequencies and a predetermined change frequency representing the frequency of the change over time of the subject. A type of change for which the change frequency can be identified without performing a frequency analysis can be exemplified by a change in the subject caused by the effect of the heart rate, a change in the subject caused by the effect of peristaltic motion of organs, or the like. The change frequency of the subject may be detected based on the output of a sensor, such as a heart rate sensor, attached to the living organism serving as the subject. The change frequency of the subject is one example of a target frequency, which is a frequency to be extracted from the images.

In the manner described above, the plurality of demodulation frequencies used by the demodulating section 200 for the demodulation may match the plurality of modulation frequencies. On the other hand, the plurality of demodulation frequencies may be at least one of the sum of and the difference between the plurality of modulation frequencies and the target frequency, such as the change frequency of the subject. In this way, the plurality of demodulation frequencies used by the demodulating section 200 for the demodulation are frequencies based on at least the modulation frequencies. In other words, by demodulating the pixel values of the plurality of images for each pixel with the plurality of demodulation frequencies based on the plurality of modulation frequencies, the demodulating section 200 generates the plurality of pieces of pixel information indicating the amounts of subject light from the subject caused by light having each of the plurality of wavelength regions, for each pixel.

The imaging information acquiring section 280 may acquire information indicating phase differences between the phase of the intensity change of at least one light among the lights having the plurality of wavelength regions and the phase at which each of the plurality of images is captured. The demodulating section 200 may then adjust the phase differences between each phase at which the plurality of images are captured and a phase of a reference signal used for demodulation to be a predetermined phase, based on the phase difference indicated by the information acquired by the imaging information acquiring section 280, and perform demodulation with the plurality of modulation frequencies for each pixel. For example, the demodulating section 200 may cause the phase differences between each phase at which the plurality of images are captured and the phase of the reference signal used for demodulation to substantially match the phase differences between the phase of the intensity change of the light and each phase at which the plurality of images are captured, and perform demodulation, with the plurality of modulation frequencies for each pixel.

The selecting section 250 may select one demodulation frequency from among the plurality of demodulation frequencies to be used in the demodulation by the demodulating section 200. For example, the demodulating section 200 may perform demodulation with the demodulation frequency selected by the selecting section 250. The selecting section 250 may select the demodulation frequency that is n times (n is an integer) the frequency of the time change of the background light, from among the plurality of demodulation frequencies. Alternatively, the selecting section 250 may select the demodulation frequency that is $2^n$ times (n is an integer) the frequency of the time change of the background light, from among the plurality of demodulation frequencies. If the modulation frequency is a rectangular wave, a harmonic wave is included in the signal, and therefore the separation capability of good when the base frequency of each modulation signal uses the $2^n$-times relationship. On the other hand, if the modulation frequency is a single frequency signal (e.g. a sine wave), sufficient separation is possible with the n-times relationship, without using the $2^n$-times relationship. The above is due to the properties of a discrete Fourier transform. If the frequency of the time change of the background light is already known, the selecting section 250 may select the demodulation frequency that is n times or $2^n$ times (n is an integer) the frequency of the time change of the background light. The frequency of the time change of the background light may be input from the outside. Furthermore, the selecting section 250 may select the demodulation frequency having the greatest distance relative to the frequency of the time change of the background light, from among the plurality of demodulation frequencies, in a case where the frequency of the time change of the background light changes over time, the frequency of the time change of the background light differs according to the location, or the like, the selecting section 250 may select the demodulation frequency that has the greatest difference relative to the frequency of the time change of the background light. As an example, the selecting section 250 may select a specified modulation frequency based on instructions from a user. For example, if instructions for displaying an image with IR light are received from the user, the selecting section 250 selects the modulation frequency f4 based on the instructions from the user.

Figure 3:
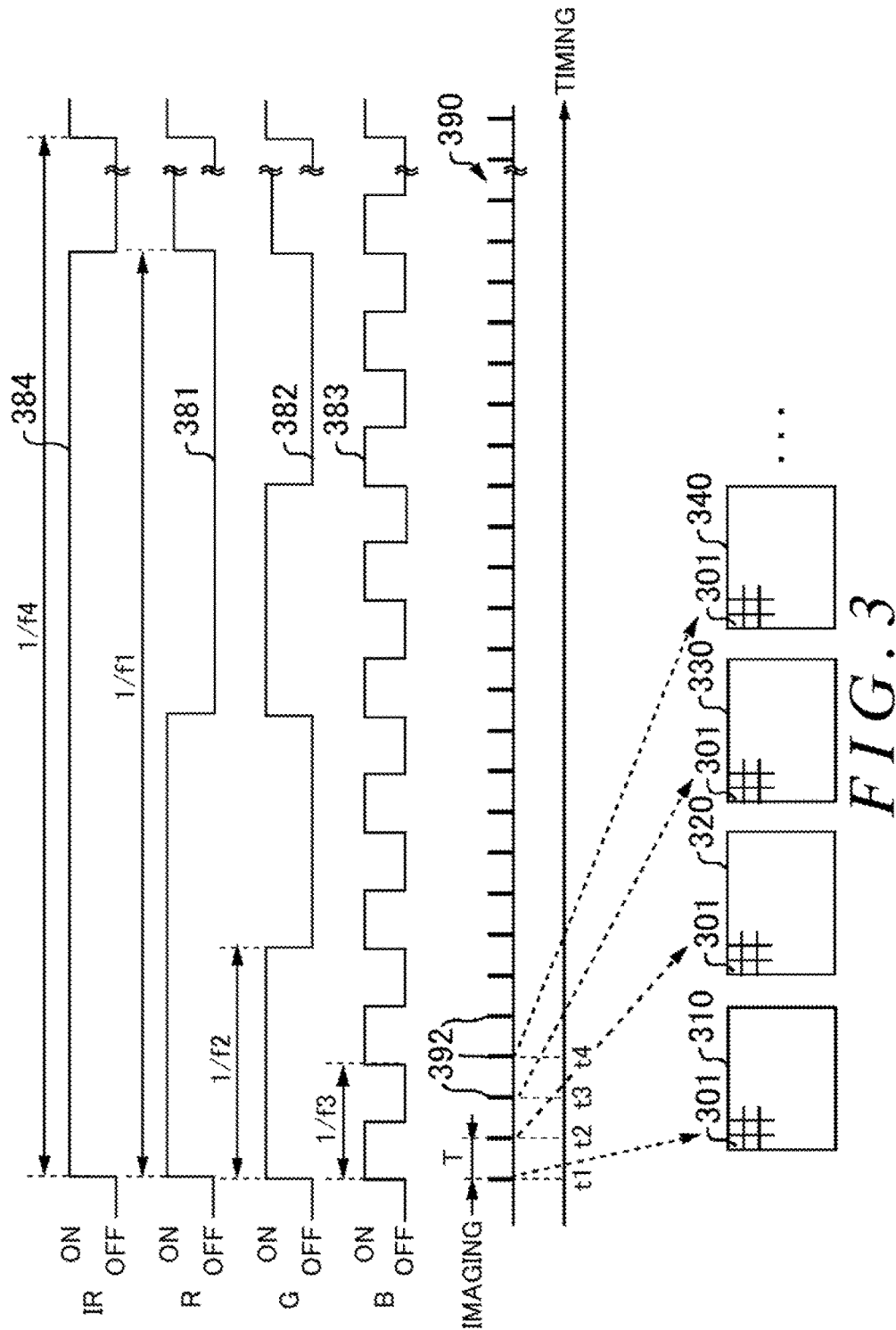
FIG. 3 shows examples of a light emission control sequence and an imaging sequence.

FIG. 3 shows examples of a light emission control sequence and an imaging sequence. The sequence 381 indicates the light emission state of the light source 131. The sequence 382 indicates the light emission state of the light source 132. The sequence 383 indicates the light emission state of the light source 133. The sequence 384 indicates the light emission state of the light source 134. Here, ON indicates a state where light is being emitted, and OFF indicates a state where light is not being emitted.

The sequence 390 indicates the imaging sequence of the imaging section 12. Each timing 392 shown in the sequence 390 indicates a timing at which an image is captured. For example, the timings 392 indicate the timings of a vertical synchronization signal. The imaging section 12 captures the images with an imaging interval T, under the control of the imaging control section 120. The imaging interval T is represented by the time between timings 392 that are temporally adjacent.

Among the modulation frequency f1, the modulation frequency f2, the modulation frequency f3, and the modulation frequency f4, the highest frequency is the modulation frequency f3. The imaging interval T of the imaging section 12 is shorter titan a modulation period 1/f3 corresponding to the modulation frequency f3. The imaging interval T is shorter than the half-period of the modulation period 1/f3. The imaging interval T may be shorter than the ⅓-period of the modulation period 1/f3. The imaging interval T may be shorter than the ¼-period of the modulation period 1/f3.

In the manner described above, a color filter for color separation is not provided between the imaging section 12 and the subject. The pixel value of one pixel 301 among the plurality of pixels of the image 310 obtained at the timing t1 can have a value corresponding to the total light amount of the R light returning from the subject as a result of the R light incident to the subject being reflected, scattered, or the like by the subject; the G light returning from the subject as a result of the G light incident to the subject being reflected, scattered, or the like by the subject; the B light returning from the subject as a result of the B light incident to the subject being reflected, scattered, or the like by the subject; and the IR light returning from the subject as a result of the IR light incident to the subject being reflected, scattered, or the like by the subject. The image 320 obtained at the tuning t2 and the image 340 obtained at the timing t4 are similar to the image 310.

At the timing t3, the B light is not radiated. Therefore, the pixel value of one pixel 301 among the plurality of pixels of the image 330 obtained at the timing t3 can have a value corresponding to the total light amount of the R light returning from the subject as a result of the IR light incident to the subject being reflected, scattered, or the like by the subject; the G light returning from the subject as a result of the G light incident to the subject being reflected, scattered, or tire like by the subject; and the IR light returning from the subject as a result of the IR light incident to the subject being reflected, scattered, or the like by the subject. In this way, each pixel value of each image can have a value corresponding to the total amount of light from the subject caused by each of the lights having the plurality of wavelength regions among the emitted lights. If there is background light that is not light from the light source 133, each pixel value of each image can have a value corresponding to the amount of light from the subject caused by the background light. In other words, each, pixel value of each image can have a value corresponding to the sum of the total amount of light from the subject caused by each of the lights having the plurality of wavelength regions from the light source 133 and the amount of light from the subject caused by the background light.

The imaging control section 120 may cause the imaging section 12 to capture each of the plurality of images in accordance with a predetermined phase relative to the intensity change of the lights having the plurality of wavelength regions. For example, if the timing of the rising of the light emission intensity of the B light is used as a reference timing, the imaging control section 120 may perform imaging in synchronization with the reference timing. In this case, the imaging control section 120 may set the imaging period T to be 1/(integer value) of 1/f3. In this way, by causing the imaging section 12 to perform imaging in accordance with a phase relative to the intensity change of the emission light, there are cases where the imaging phase difference is taken into consideration and the reference waveform does not need to be adjusted when the demodulating section 200 performs demodulation.

The imaging control section 120 outputs information indicating the imaging order and imaging timing of each image, to the imaging information output section 150. The light emission control section 140 outputs information indicating the light emission timing of each light source of the light emitting section 130 to the imaging information output section 150. The light emission control section 140 outputs information indicating the timing of which the light emitting section 130 starts the modulation of the emission light intensity of each light source, to the imaging information output section 150. The light emission control section 140 outputs information indicating the emission light intensity of each light source of the light emitting section 130 to the imaging information output section 150. The imaging information output section 150 outputs to the image processing unit 40, in association with the images, these pieces of information, acquired from the light emission control section 140 and the imaging control section 120. In this way, in the image processing unit 40, the demodulating section 200 can perform accurate demodulation using the information associated with the images, furthermore, the image generating section 220 can generate images with suitable luminance, based on the emission light intensity and the like of each light source.

In the present embodiment, modulation frequencies of the B light, the G light, the R light, and the IR light are highest to lowest in the stated order. However, the modulation frequencies may be suitably determined according to the observation target. For example, if there is a desire to acquire a red image with higher time resolution, the modulation frequency of the R light may be made higher than the modulation frequencies of the other lights.

Figure 4A:
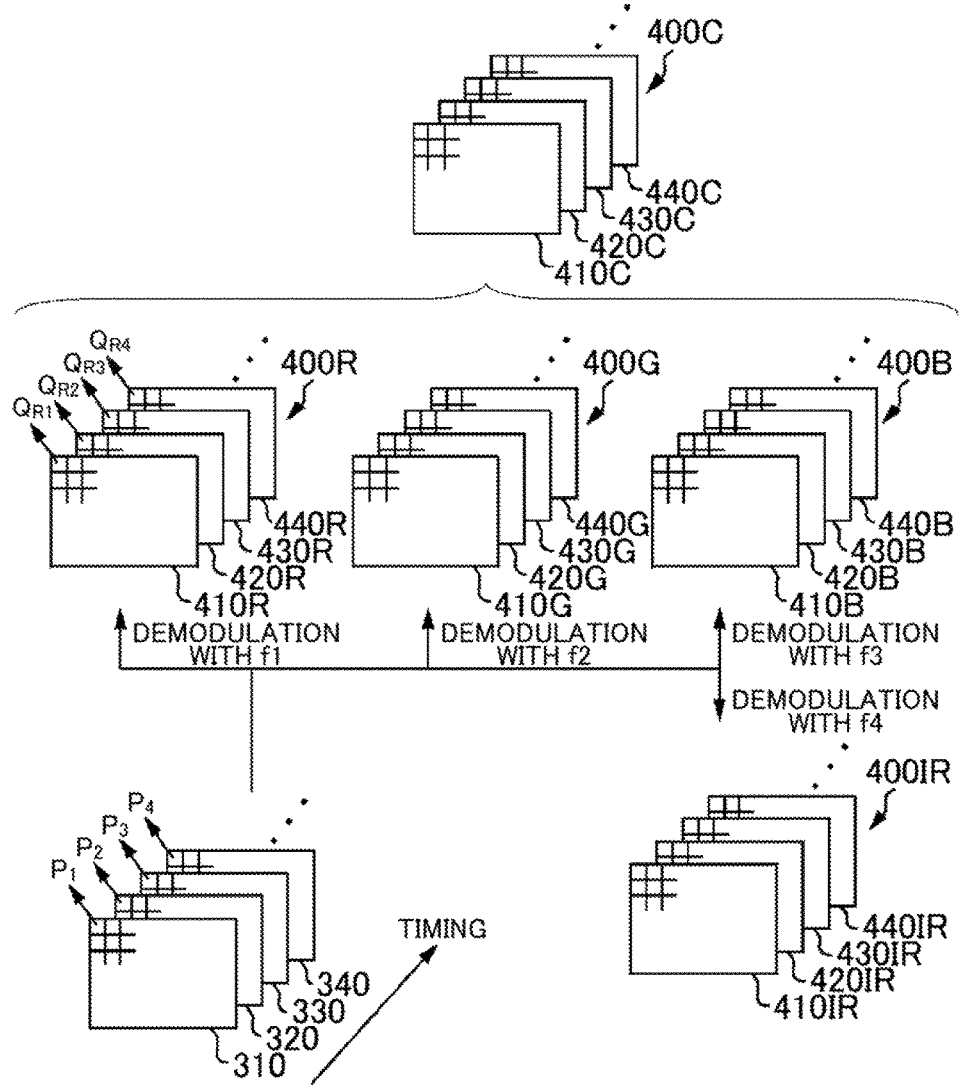
FIG. 4A schematically shows image processing of the image processing unit 40.

FIG. 4A schematically shows image processing of the image processing unit 40.

The demodulating section 200 generates a plurality of images including an image 410R, an image 420R, an image 430R, an image 440R, etc. by demodulating a plurality of images include an image 310, an image 320, an image 330, and an image 340, etc. with the demodulation frequency f1 for each pixel. For example, the demodulating section 200 generates discrete time series data including a pixel value QR1 of the pixel 301 of the image 410R, a pixel value QR2 of the pixel 301 of the image 420R, a pixel value QR3 of the pixel 301 of the image 430R, a pixel value QR4 of the pixel 301 of the image 440R, etc. by demodulating, with the modulation frequency f1, discrete time series data, including a pixel value P1 of the pixel 301 in the image 310, a pixel value P2 of the pixel 301 in the image 320, a pixel value P3 of the pixel 301 in the image 330, a pixel value P4 of the pixel 301 in the image 340, etc. The details of the demodulation process are described further below with relation to FIG. 5. The demodulating section 200 generates the pixel value of each pixel of the image 410R, the image 420R, the image 430R, the image 440R, etc. by applying a similar process to these other pixels.

Furthermore, the demodulating section 200 generates a plurality of images including an image 410G, an image 420G, an image 430G, an image 440G, etc. by demodulating a plurality of images include an image 310, an image 320, an image 330, and an image 340, etc. with the demodulation, frequency 12 for each pixel. The demodulating section 200 generates a plurality of images including an image 410B, an image 420B, an image 430B, an image 440B, etc. by demodulating a plurality of images include an image 310, an image 320, an image 330, and an image 340, etc. with the demodulation frequency f3 for each pixel. The demodulating section 200 generates a plurality of images including an image 410IR, an image 420IR, an image 430IR, an image 440IR, etc. by demodulating a plurality of images include an image 310, an image 320, an image 330, and an image 340, etc. with the demodulation frequency f4 for each period. The processing performed by the demodulating section 200 to generate these images is the same as the processing based on image 410R, the image 420R, the image 430R, and the image 440R, except that the processing based on the demodulation frequency is different. Therefore, a description of the details of the processing for generating these images is omitted.

The image generating section 220 generates a visible light image group 400C, which is an image group forming a colorized visible light moving image, from the image group 400R, the image group 400G, and the image group 400B. Specifically, the image generating section 220 generates an image 410C containing each color component, from the image 410R, the image 410G, and the image 410B. Similarly, the image generating section 220 generates an image 420C containing each color component, from the image 420R, the image 420G, and the image 4206. Similarly, the image generating section 220 generates an image 430C containing each color component, from the image 4308, the image 430G, and the image 430B. Similarly, the image generating section 220 generates an image 440C containing each color component, from the image 440R, the image 440G, and the image 440B. The image 410C, the image 420C, the image 430C, and the image 440C may be images that form a colorized visible light moving image. The image generating section 220 may generate image data of the visible light image group 400C expressed as a luminance signal and a color differential signal for processing at later stages. For example, when generating video signal information for display, the image generating section 220 generates YUV component signal information. When generating image data for storage, the image generating section 220 generates YCrCb image data from the visible light image group 400, and performs a moving image compression process. Furthermore, the image generating section 220 generates images included in the image group 400IR, as images forming a moving image resulting from infrared light.

Figure 4B:
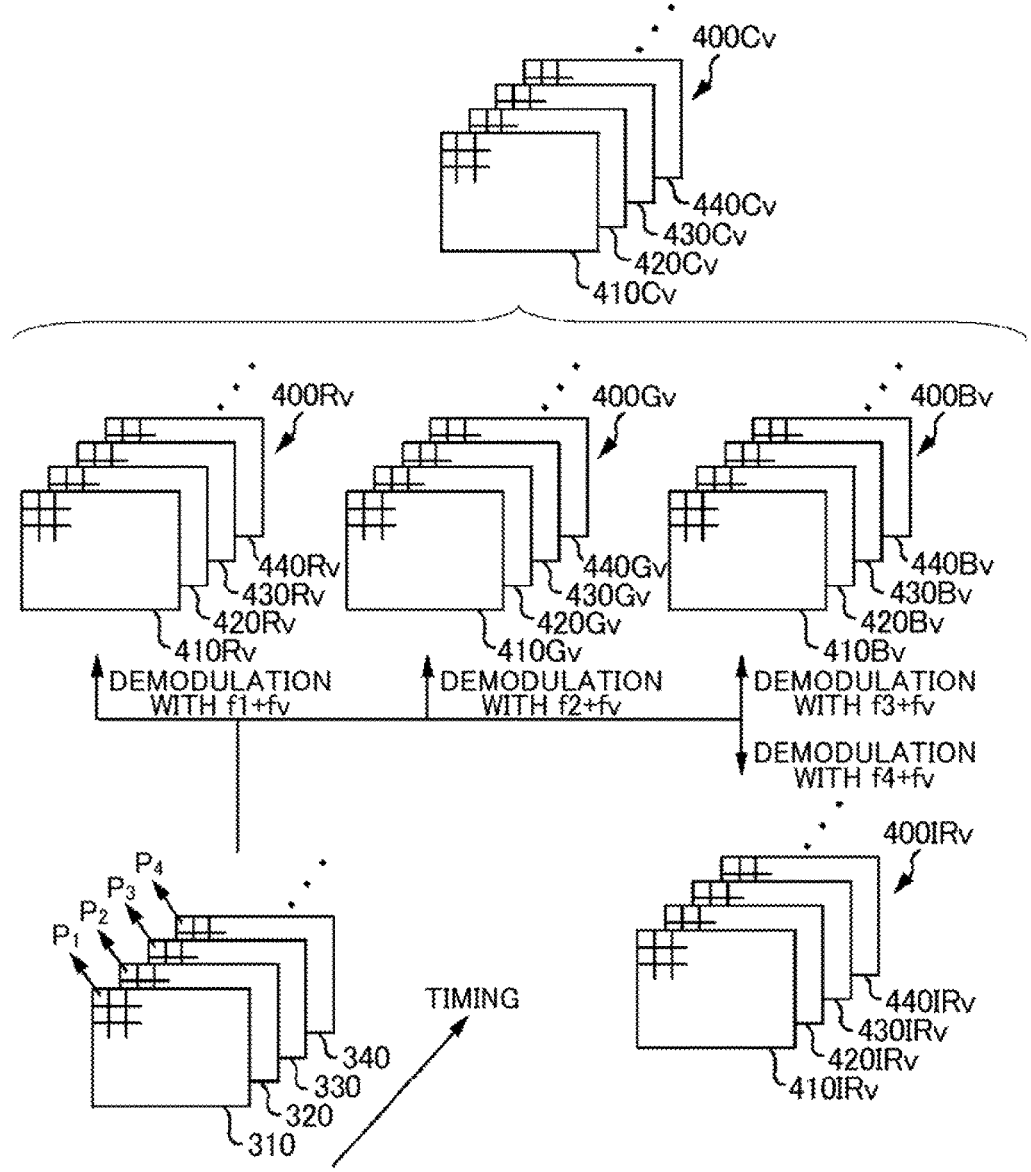
FIG. 4B schematically shows image processing relating to the change frequency specifying section 240.

FIG. 4B schematically shows image processing relating to the change frequency specifying section 240.

The change frequency specifying section 240 specifies the change frequency fv representing the movement or the like of the subject, by performing a frequency analysis on the pixel values of the image 410R, the image 420R, the image 430R, the image 440R, etc., for example. As an example, the change frequency specifying section 240 separates the frequency components of she time series signal formed by the pixel values of a specified pixel in the image 410R, the image 420R, the image 430R, the image 440R, etc., and determines the frequency of the frequency component amount exceeding a predetermined threshold value to be the change frequency fv.

The demodulating section 200 generates a plurality of images including an image 410Rv, an image 420Rv, aa image 430Rv, an image 440Rv, etc. by demodulating the plurality of images including the image 310, the image 320, the image 330, the image 340, etc. with the modulation frequency f1+fv for each pixel. Furthermore, the demodulating section 200 generates a plurality of images including an image 410Gv, an image 420Gv, and image 430Gv, an image 440Gv, etc. by demodulating the plurality of images including the image 310, the image 320, the image 330, the image 340, etc. with the modulation frequency f2+fv for each pixel. The demodulating section 200 generates a plurality of linages including an image 410Bv, as image 420Bv, an image 430Bv, an image 440Bv, etc. by demodulating the plurality of images including the image 310, the image 320, the image 330, the image 340, etc. with the modulation frequency f3+fv for each pixel. The demodulating section 200 generates a plurality of images including an image 410IRv, as image 420IRv, an image 430IRv, an image 440IRv, etc. by demodulating the plurality of images including the image 310, the image 320, the image 330, the image 340, etc. with the modulation frequency f4+fv for each pixel. The processing performed by the demodulating section 200 to generate these images is the same as the processing for generating, the image 410R, the image 420R, the image 430R, and the image 440R, except that the processing based on the demodulation frequency is different. Therefore, a description of the details of the processing for generating these images is omitted.

The image generating section 220 generates a visible light image group 400Cv, which is an image group forming a colorized visible light moving image representing the movement of the subject, from the image group 400Rv the image group 400Gv, and the image group 400Bv. Specifically, the image generating section 220 generates an image 410Cc containing each color component, from the image 410Rv, the image 410Gv, and the image 410Bv. Similarly, the image generating section 220 generates an image 420Cv containing each color component, from the image 420Rv, the image 420Gv, and the image 420Bv. Similarly, the image generating section 220 generates an image 430Cv containing each color component, from the image 430Rv, the image 430Gv, and the image 430Bv. Similarly, the image generating section 220 generates an image 440Cv containing each color component, from the image 440Rv, the image 440Gv; and the image 440Bv. The image 410Cv, the image 420Cv, the image 430Cv, and the image 440Cv may be frame images that form a colorized visible light moving image representing movement of the subject. Furthermore, the image generating section 220 generates images included in the image group 400IRv, as images forming a moving image resulting from infrared light.

The change frequency specifying section 240 may specify the change frequency fv by performing a frequency analysis on the pixel values for each of the plurality of pixels of the image 410R, the image 420R, the image 430R, the image 440R, etc. Furthermore, the change frequency specifying section 240 may perform the pixel value frequency analysis for each pixel. In addition, the change frequency specifying section 240 may specify the change frequency fv by performing a frequency analysis on a time series signal formed by the average values of predetermined plurality of pixels.

Here, a case is described in which f1+fv is used as the demodulation frequency used for the demodulation process for generating the image group 400Rv. However, f1−fv may instead be used as the demodulation frequency used for the demodulation process for generating the image group 400Rv. Similarly, f2−fv may instead be used as the demodulation, frequency used for the demodulation process for generating the image group 400Gv. Similarly, f3−fv may instead be used as the demodulation frequency used for the demodulation process tor generating the image group 400Bv. Similarly, f4−fv may instead be used as the demodulation frequency used for the demodulation process for generating the image group 400IRv. FIG. 4B shows the process performed when one change frequency fv is specified. If a plurality of change frequencies are specified, images may be generated for each change frequency by performing demodulation with the modulation frequencies and the demodulation frequencies based on the modulation frequencies, for each of the plurality of change frequencies.

Figure 5:
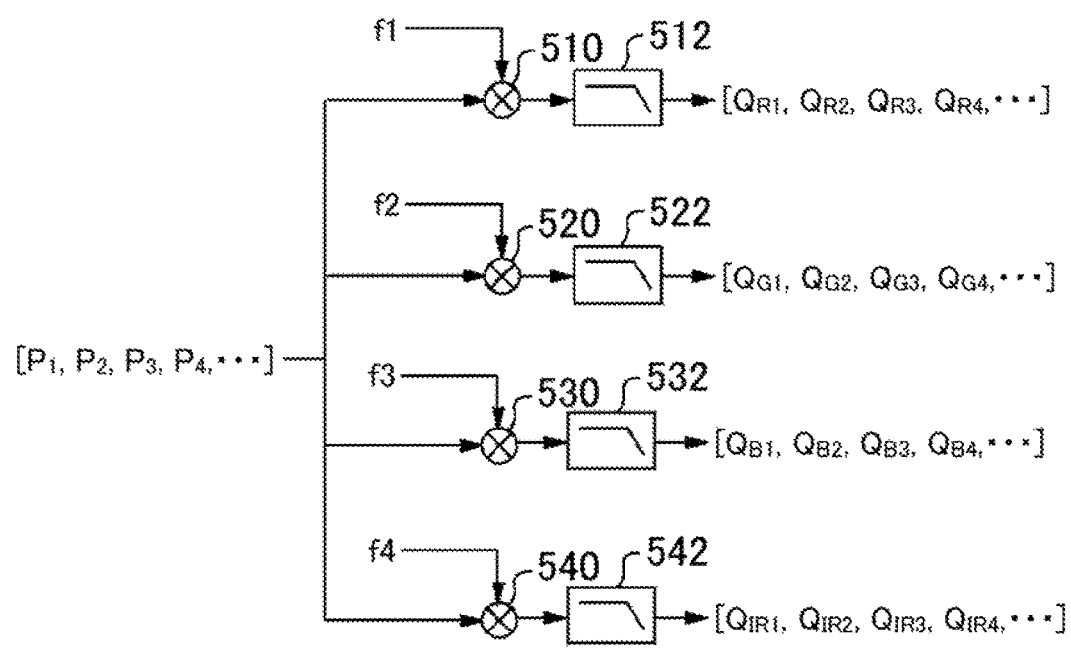
FIG. 5 schematically shows processing of a pixel unit by the demodulating section 200.

FIG. 5 schematically shows processing of a pixel unit by the demodulating section 200. The process described here is for the pixel value time series data Pk (k=1, 2, 3, 4, . . . ) of a single pixel 301.

The demodulating section 200 performs multiplication 510 between the time series data formed by P1, P2, P3, P4, etc. and the time series data of the reference waveform of the change frequency f1. The demodulating section 200 then applies a frequency filter 512 to the time series data obtained as a result of the multiplication 510, thereby generating the time series data QR1, QR2, QR3, QR4, etc, of the red pixel value. The frequency filter 512 preferably includes a frequency characteristic that substantially cuts off the frequency component of the frequency that is the difference between the modulation frequency f1 and another modulation frequency and the frequency component of the frequency that is the sum of the modulation frequency f1 and another modulation frequency. The frequency filter 512 may be a low-pass filter.

Similarly, the demodulating section 200 performs multiplication 520 between the time series data Pk and the time series data of the reference waveform of the change frequency f2. The demodulating section 200 then applies a frequency filter 522 to the time series data obtained as a result of the multiplication 520, thereby generating the time series data QG1, QG2, QG3, QG4, etc. of the green pixel value. The frequency filter 522 preferably includes a frequency characteristic that substantially cuts off the frequency component of the frequency that is the difference between the modulation frequency f2 and another modulation frequency and the frequency component of the frequency that is the sum of the modulation frequency f2 and another modulation frequency. The frequency filter 522 may be a low-pass filter.

Furthermore, the demodulating section 200 preforms multiplication 530 between the time series data Pk and the time series data of the reference waveform of the change frequency f3. The demodulating section 200 then applies a frequency fiber 532 to the time series data obtained as a result of the multiplication 530, thereby generating the time series data QB1, QB2, QB3, QB4. etc. of the blue pixel value. The frequency filter 532 preferably includes a frequency characteristic that substantially cuts off the frequency component of the frequency that is the difference between the modulation frequency f3 and another modulation frequency and the frequency component of the frequency that is the sum of the modulation frequency f3 and another modulation frequency. The frequency filter 532 may be a low-pass filter.

Furthermore, the demodulating section 200 performs multiplication 540 between the time series data Pk and the time series data of the reference waveform of the change frequency f4. The demodulating section 200 then applies a frequency filter 542 to the time series data obtained as a result: of the multiplication 540, thereby generating the time series data QIR1, QIR2, QIR3, QIR4, etc. of the infrared pixel value. The frequency filter 542 preferably includes a frequency characteristic that substantially cuts off the frequency component of the frequency that is the difference between the modulation frequency f4 and another modulation frequency and the frequency component of the frequency that is the sum of the modulation frequency f4 and another modulation frequency. The frequency filter 542 may be a low-pass filter.

The demodulating section 200 preferably uses time series data with a phase substantially the same as the phase of the intensity change of the R light, as the time series data of the change frequency f1 used in the multiplication 510. For example, the difference between the rising timing of the intensity change of the R light and the imaging timing t1 is preferably caused to substantially match the difference between the rising timing of the reference waveform indicated by the time series data, used in the multiplication 510 and the timing at which the image 410 is captured in this reference waveform. In other words, the phase of the reference signal in the demodulation process is preferably caused to match the phase of the modulation signal. Similarly, the demodulating section 200 preferably uses time series data with a phase substantially the same as the phase of the intensity change of the G light, as the time series data of the change frequency f2 used in the multiplication 520. The demodulating section 200 preferably uses time series data with a phase substantially the same as the phase of the intensity change of the B light, as the time series data of the change frequency f3 used in the multiplication 530. The demodulating section 200 preferably uses time series data with a phase substantially the same as the phase of the intensity change of the IR light, as the time series data of the change frequency f4 used in the multiplication 540.

FIG. 5 is used to describe processing of the demodulating section 200 for the time series data Pk of the pixel values for the pixel 301 at a specified position in the image. By applying a similar process to the pixel values of a pixel at an arbitrary positon (i, j) in the image, the demodulating section 200 can acquire the time data series data of the pixel values corresponding to each wavelength region at the arbitrary position (i, j).

Furthermore, FIG. 5 is used to describe a case in which the demodulating section 200 applies the modulation frequencies as the demodulation frequencies. When generating an image in which the red pixel values represent change of the subject, for the time series data Pk, the demodulating section 200 only needs to apply f1+fv as the demodulation frequency and apply similar multiplication and a similar frequency filter. Furthermore, when generating an image in which the green pixel values represent change of the subject, for the time series data Pk, the demodulating section 200 only needs to apply f2+fv as the demodulation frequency and apply similar multiplication and a similar frequency filter. When generating an image in which the blue pixel values represent change of the subject, for the time series data Pk, the demodulating section 200 only needs to apply f3+fv as the demodulation frequency and apply similar multiplication and a similar frequency filter. When generating an image in which the infrared pixel values represent change of the subject, for the time series data Pk, the demodulating section 200 only needs to apply f4+fv as the demodulation frequency and apply similar multiplication and a similar frequency filter.

With the imaging system 5 described above, it is possible to acquire images caused by lights having a plurality of wavelength regions, by multiplexing lights that are intensity-modulated with modulation frequencies differing for each wavelength and irradiating the subject. Therefore, it is possible to acquire images based on lights having the plurality of wavelength regions, without radiating the irradiation light with time separation for each wavelength region and without performing imaging with the light of each wavelength region with time separation. Furthermore, there is no need to perform wavelength separation for each pixel with a color filter or the like in the imaging element. Therefore, it is possible to perform imaging of the subject with high resolution. In this way, it is possible to miniaturize the imaging apparatus.

Figure 6:
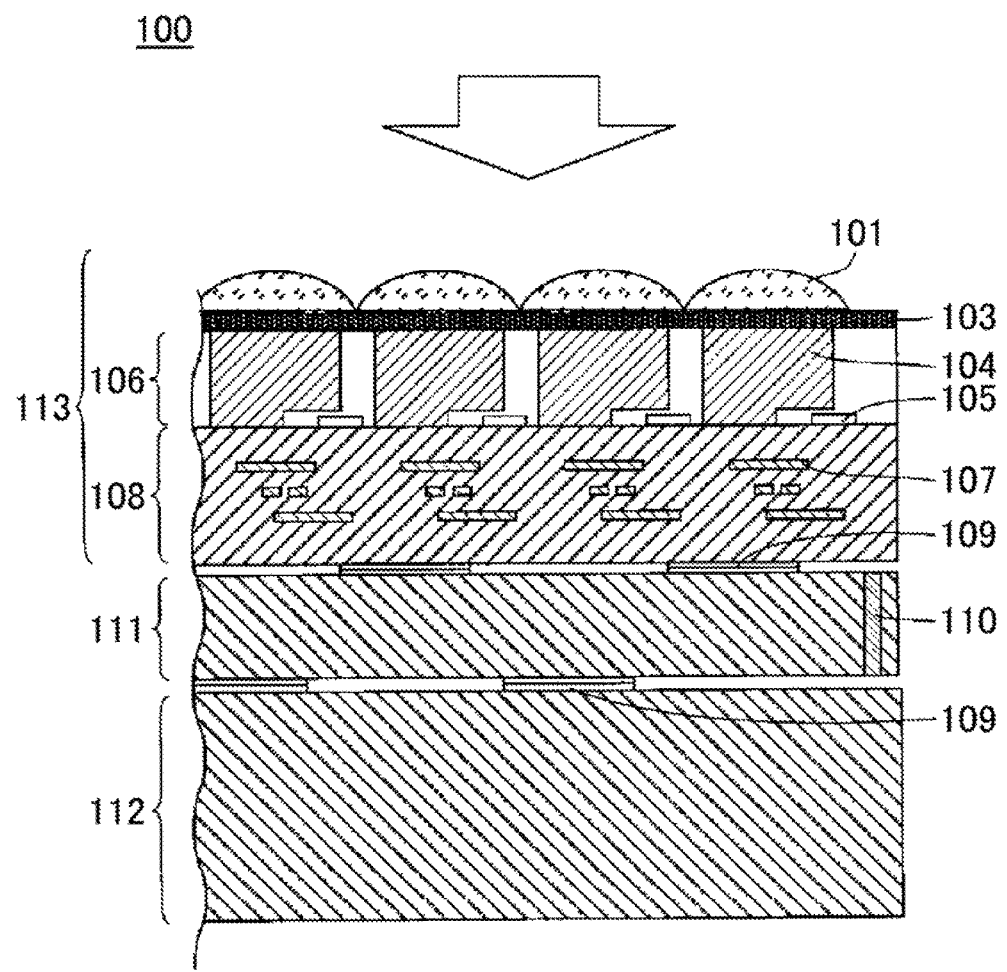
FIG. 6 is a cross-sectional view of an imaging element 100 that is a modification of the imaging element 10.

FIG. 6 is a cross-sectional view of an imaging element 100 that is a modification of the imaging element 10. The imaging element 100 is a backside illumination imaging element. The imaging element 100 includes an imaging chip 113 that outputs a pixel signal corresponding to the incident light, a signal processing chip 111 that processes the pixel signal, and a memory chip 112 that stores she pixel signal. The imaging chip 113, the signal processing chip 111, and the memory chip 112 are layered, and are electrically connected to each other by bumps 109 that are conductive and made of Cu or the like.

As shown in the drawing, the incident light is mainly incident in the direction indicated by the white arrow. In the present embodiment, the surface of the imaging chip 113 to which the incident light is incident is referred to as the back surface.

The imaging chip 113 is a backside illumination MOS image sensor, for example. The photodiode layer 106 is arranged on the back surface side of the wiring layer 108. The photodiode layer 106 includes a plurality of photodiodes 104 arranged two-dimensionally and transistors 105 provided corresponding to the photodiodes 104. A set of a photodiode 104 and a transistor 105 forms one pixel element.

Microlenses 101 are provided on the side of the photodiode layer 106 to which the incident light is incident, with a passivation film 103 interposed therebetween. The microlenses 101 are provided to correspond respectively to the pixels. Each microlense 101 focuses the incident light toward the corresponding photodiode 104.

The wiring layer 108 includes wiring 107 that transmits the pixel signals from the photodiode layer 106 to the signal processing chip 111. The wiring 1074 may be multilayered, and passive elements and active elements may be provided.

A plurality of the bumps 109 are provided on the wiring layer 108. These bumps 109 are aligned with a plurality of bumps 109 provided on the surface of the signal processing chip 111 opposite thereto, and the aligned humps 109 are bonded to each other as a result of pressure or the like being applied to the imaging chip 113 and the signal processing chip 111 to form an electrical connection.

In the same manner, a plurality of bumps 109 are formed on the surfaces of the signal processing chip 111 and the memory chip 112 that face each other. These bumps 109 are aligned with each other, and the aligned bumps 109 are bonded to each other as a result of pressure or the like being applied to the signal processing chip 111 and the memory chip 112 to form an electrical connection. The bonding between the bumps 109 is not limited to Cu bump bonding caused by solid phase diffusion, and may instead be micro bump bonding caused by solder fusion. In this way, the imaging chip 113 and the signal processing chip 111 that includes the processing circuits are electrically connected with a layered structured.

The signal processing chip 111 includes a silicon penetration electrode 110 that connects the circuits provided on the front and back surfaces thereof to each other. The silicon penetration electrode 110 is preferably provided in a peripheral region. Alternatively, the silicon penetration electrode 110 may be provided in the peripheral region of the imaging chip 113 or in the memory chip 112.

The signal processing chip 111 includes a signal processing circuit that processes she pixel signals from the photodiode layer 106. For example, the signal processing chip 111 includes a signal processing circuit that performs column amplification, correlated doable sampling (CDS), and analog/digital (A/D) conversion. The pixel signals from the photodiode 104 undergo amplification, CDS, and A/D conversion by the signal processing circuit of the signal processing chip 111. In this way, with the imaging element 100, it is possible to provide the signal processing chip 111 with a column amplifier, a CDS circuit, and an AD conversion circuit. As a result, it is possible to provide a large number of column amplifiers, CDS circuits, and AD converters. Therefore, it is possible to perform high-speed processing on the analog pixel signals output by the photodiode 104. Accordingly, it is possible to shorten the imaging period for the images.

The memory chip 112 includes a pixel memory corresponding to each pixel. The pixel signals that have been A/D converted by the signal processing chip 111 are stored in the pixel memory of the memory chip 112.

The signal processing chip 111 includes a computational circuit that processes the pixel signals stored in the pixel memory. The computational circuit of the signal processing chip 111 may have a function to perform at least a portion of the processing of the image processing unit 40. For example, the computational circuit of the signal processing chip 111 may have a function to perform at least a portion of the process of the imaging information acquiring section 280, the demodulating section 200, the change frequency specifying section 240, the selecting section 250, and the image generating section 220. In this way, the computational circuit of the signal processing chip 111 may perform at least a portion of the process for perforating the frequency separation based on the modulation frequencies for multiplexing the emitted light. The computational circuit of the signal processing chip 111 may perform data, compression on the pixel signals, and output the result. In this way, it is possible to reduce the load of the input/output interface of the pixel signals. It should be noted that the computational circuit may be provided in the memory chip 112.

In this way, with the imaging element 100, the imaging chip 113, the signal processing chip 111 including the processing circuit and the memory chip 112 are layered three-dimensionally with a layered structured. Therefore, it is possible to hold the pixel signals and perform signal processing on the pixel signals in the signal processing chip 111 and the memory chip 112 near the imaging chip 113. In this way, it is possible to increase the speed of reading the pixels and to reduce the amount of data output from the imaging element 100. Furthermore, it is possible to reduce the load at later stages of the imaging element 100. Accordingly, it is possible to shorten the imaging period for the images.

In the imaging system 5 described above, the subject is imaged using R light G light, B light, and IR light. However, the light used for imaging is not limited to a combination of R light, G light, B light, and IR light. Lights with combinations of various wavelength regions can be adopted as the light used for imaging. It should be noted that a portion of the wavelength region of a certain light used for the imaging may overlap with the wavelength region of another light. Furthermore, the wavelength region of a certain light used for the imaging may be a partial wavelength region of the wavelength region of another light. In this way, the subject may be irradiated by lights with partially overlapping wavelength regions that have been intensity-modulated with a plurality of modulation frequencies.

The wavelength region of a certain light used for the imaging may overlap with the entire range of the wavelength region of another light. For example, IR lights having the same wavelength regions may be modulated with different modulation frequencies from each other and used to irradiate the subject. As an example, in the imaging system 5, the subject may be irradiated with, in addition to first IR light that is intensity-modulated with the modulation frequency f4, second IR light that has the same wavelength, region as the first IR light and is intensity-modulated with a modulation frequency f5 that is different from the modulation frequency f4. Furthermore, white lights may be modulated with different modulation, frequencies from each other and used to irradiate the subject. In this way, the subject may be irradiated with lights that are intensity-modulated with a plurality of modulation frequencies, and that have wavelength regions that entirely overlap. Lights that have identical wavelength regions but are intensity-modulated with different modulation frequencies are one example of lights that have different characteristics from each other. In this way, redundancy is realized with regard to the wavelength regions of the lights irradiating the subject and the subject may be irradiated with lights that have the same wavelength and are intensity-modulated with modulation frequencies that are different from each other.

In this way, the subject may be irradiated with lights that have matching wavelength regions and are intensity-modulated with a plurality of modulation frequencies. Here, "matching wavelength regions" includes not only wavelength regions whose upper limit values and lower limit values are matching, but also whose upper limit values and lower limit values are substantially matching. "Substantially matching" has a scope including an error caused by variation between apparatuses. Furthermore, "matching wavelength regions" has a scope that includes lights without a range limit on the wavelength region, such as white lights, having overlapping wavelength region. In addition, lights with "matching wavelength regions" may have optical spectra in the wavelength region that are all matching or that are different. In the wavelength region, the peak wavelengths of the irradiation intensity may be the same or may be different. If lights with matching wavelength regions irradiate the subject, light from a single light source may be intensity-modulated by the sum of the modulations signals with a plurality of modulation frequencies, or lights from a plurality of light sources that emit lights with matching wavelength regions may be intensity-modulated with different modulation frequencies.

Here, a detailed description of one example of the operation of the imaging system 5 in a case where lights having the same wavelength regions are multiplexed and used to irradiate the subject is provided, in which the subject is irradiated with IR light intensity-modulated with the modulation frequency f4 and IR light intensity-modulated with the modulation frequency f5. The light emission control section 140 drives a single light source 134 according to a modulation intensity obtained by combining the modulation frequency f4 and the modulation frequency f5, thereby causing the light source 134 to generate IR light obtained by multiplexing the IR light intensity-modulated with the modulation frequency f4 and the IR light intensity-modulated with the modulation frequency f5 from the light source 134. Instead of generating the multiplexed IR light from a single light source 134, a separate light source may be added to generate the IR light intensity-modulated with the modulation frequency f5.

In the image processing unit 40, the selecting section 250 selects whether to generate the pixel information indicating the subject light amount from the subject caused by the light intensity-modulated with the modulation frequency f4 or to generate the pixel information indicating the subject light amount from the subject caused by the light intensity-modulated with the modulation frequency f5. For example, from among the modulation frequency f4 and the modulation frequency f5, the selecting section 250 selects the frequency whose difference relative to the optical disturbance frequency is greater than a predetermined value as the demodulation frequency. Specifically, from among the modulation frequency f4 and the modulation frequency f5, the selecting section 250 selects the modulation frequency whose difference relative to the frequency of the time change of the background light is greater as the demodulation frequency. If the modulation frequency f4 is a frequency that matches or is close to the frequency of the time change of the background light, the selecting section 250 selects f5 as the demodulation frequency. In this case, the demodulating section 200 performs demodulation with f5. The image generating section 220 then generates the image caused by the light from the subject resulting from the RI light intensity-modulated with the modulation frequency f5, based on the pixel information of each pixel generated by the demodulation performed by the demodulating section 200 with f5. The frequency of the time change of the background light may be specified based on the pixel information of the image of the background light generated by the image generating section 220. Furthermore, the frequency of the time change of the background light may be input from outside of the imaging system 5, and may be designated by the user.

If the modulation frequency matches or is close to the frequency of the time change of the background light, the effect of the background light is included in the pixel information acquired by performing demodulation, with a demodulation frequency that matches this modulation frequency. Therefore, there are cases where the S/N ratio of the pixel information resulting from the IR light is undesirably low. However, as described above, by having the selecting section 250 select a frequency that is distanced from the frequency of the time change of the background light, it is possible to generate an image using pixel information with a higher S/N ratio. By having a redundancy for the wavelength of the light irradiating the subject, it is possible to increase the tolerance with respect to optical disturbance. Here, a case is described in which irradiation is performed using light intensity-modulated with two modulation frequencies as a redundancy, but the illumination may be preformed using light intensity-modulated with three or more modulation frequencies. In this case, the selecting section 250 may select, from among the three or more modulation frequencies, the frequency whose difference with respect to the frequency of the time change of the background light is greatest as the demodulation frequency.

Figure 7:
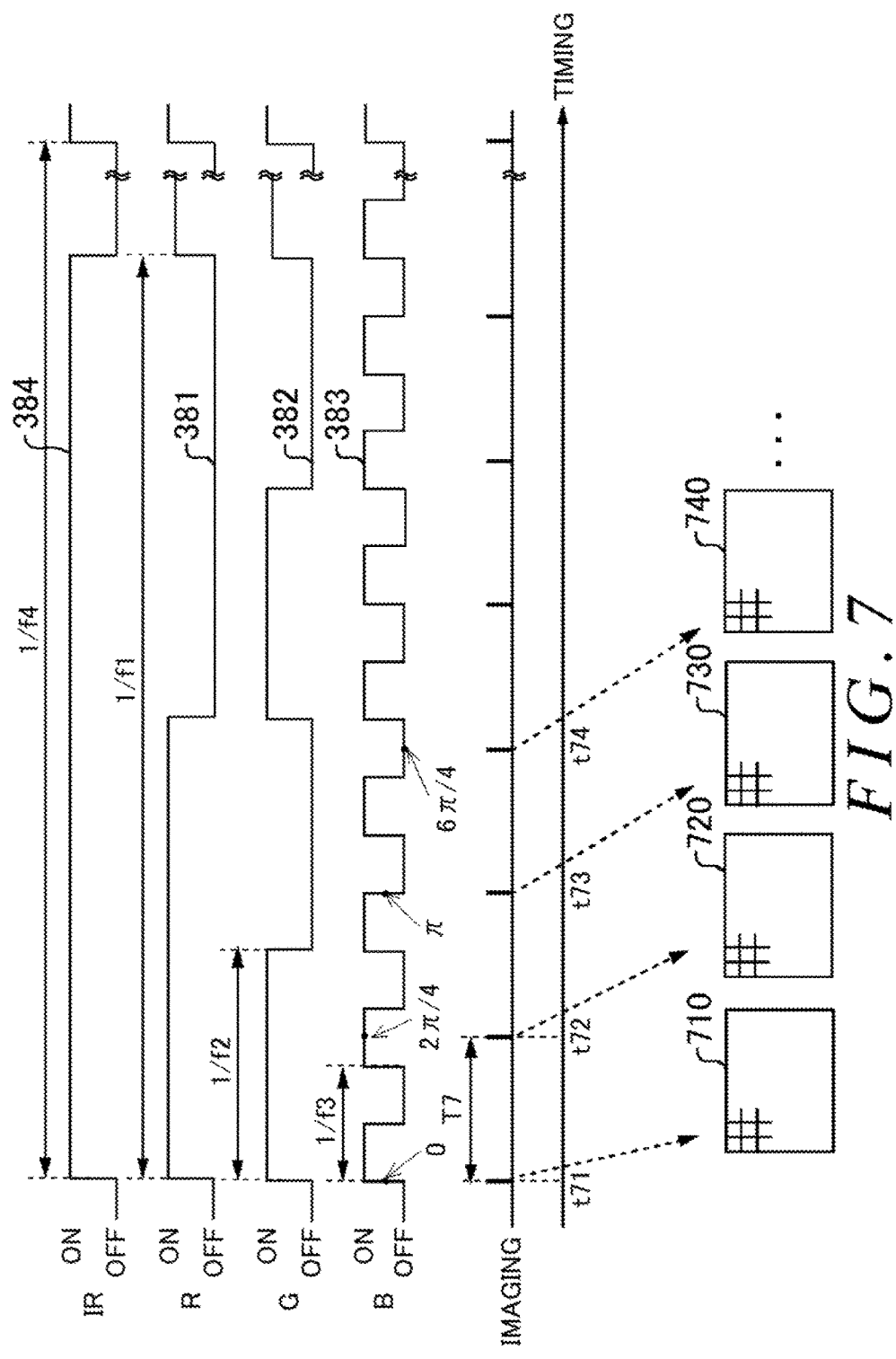
FIG. 7 shows a modification of the imaging sequence along with the light emission control sequence.

FIG. 7 shows a modification of the imaging sequence along with the light emission control sequence. FIG. 7 shows an imaging sequence for effectively generating the pixel information by having the demodulating section 200 perform demodulation with the modulation frequency f3 while making the imaging interval longer than the period 1/f3 corresponding to the modulation frequency f3. Specifically, FIG. 7 shows an imaging sequence in a case where the imaging interval T7 is set to 1/f3+1/(4×f3).

With the timing t71 in one period of the period 1/f3 corresponding to the phase 0, the timing t72 corresponds to the phase 2π/4, the timing t73 corresponds to the phase π, and the timing t74 corresponds to the phase 6π/4. Therefore, according to the present imaging sequence, in one period of the period 1/f3, imaging is performed effectively four times at different phases. Therefore, the demodulating section 200 performs demodulation with the demodulation frequency f3 while treating the image 710, the image 720, the image 730, and the image 740 captured at the timing t71, the timing t72, the timing t73, and the timing t74 respectively as images captured at the phase 0, the phase 2π/4, the phase π, and the phase 6π/4 in one period. In this way, it is possible to effectively generate the pixel information of the B image by performing demodulation with the modulation frequency f3 while making the imaging interval longer than the period 1/f3.

Various values other than an integer multiple of 1/f3 can be adopted as the imaging interval T7. It should be noted that, with N as a positive number, if the timing interval T7 matches (N+½)/f3, the phase of the imaging tuning is preferably shifted from the rising of the irradiation light such that the imaging timing does not substantially match the rising of the illumination light.

FIG. 7 is used to describe a case in which the imaging control section 120 performs imaging with a frequency lower than f3. However, the imaging control section 120 may perform imaging with a frequency lower than any one of the modulation frequency f1, the modulation frequency f2, and the modulation frequency f4. Furthermore, the imaging control section 120 may perform the imaging with a frequency lower than any one of the modulation frequency f1, the modulation frequency f2, the modulation frequency f3, and the modulation frequency f4.

The imaging system 5 described above uses light intensity-modulated with a plurality of single modulation frequencies such as the modulation frequencies f1, f2, f3, and f4 as the irradiation light, and the demodulating section 200 demodulates the pixel values with a plurality of single demodulation frequencies. However, in the imaging system 5, instead of light modulated with a plurality of prescribed modulation frequencies, light intensity-modulated with a plurality of modulation frequency bands may be used. In this case, in the descriptions of the imaging system 5 above, it is possible to replace the term "modulation frequency" with the term "modulation frequency band." Light intensity-modulated with a modulation frequency band may be light that is intensity-modulated with an arbitrary frequency associated with a modulation frequency band having a certain width (e.g. from 90 Hz to 110 Hz. or the like). If light intensity-modulated with a plurality of modulation frequency bands is used as the irradiation light, the demodulating section 200 may demodulate the pixel values with a specified plurality of demodulation frequencies based on the modulation frequency band. Furthermore, light intensity-modulated with single modulation frequencies and light intensity-modulated with modulation frequency bands may be mixed together. In other words, the term "a plurality of modulation frequencies or modulation frequency bands" indicates being made up of one or both of single-modulation frequencies and modulation frequencies having a certain width.

Furthermore, instead of a specified plurality of demodulation frequencies, the demodulating section 200 may demodulate the pixel values with a plurality of demodulation frequency bands. In a case of demodulating the pixel values with a plurality of demodulation frequency bands, when the irradiation light is intensity-modulated with the plurality-of-specified modulation frequencies, the demodulating section 200 may perform demodulation with a plurality of demodulation frequency bands based on the plurality of specified modulation frequencies. On the other hand, when the irradiation light is intensity-modulated with a plurality of specified modulation frequency bands, the demodulating section 200 may perform demodulation with a frequency band based on the plurality of specified modulation frequency bands.

The following describes, as one example, the basics of an operation in a ease where light intensity-modulated with a plurality of modulation frequency bands is used as the irradiation light. By having the light emission control section 140 intensity-modulate the light from the light emitting section 130 with a plurality of modulation frequency bands, light intensity-modulated with a plurality of modulation frequency bands is emitted from the light emission control section 140, the light emitting section 130, and the light guide 22. The imaging information output section 150 outputs a plurality of images of the subject captured by the imaging section 12 to the image processing unit 40, in association with the information indicating the plurality of modulation frequency bands, in this case, information indicating the phase differences between the phase of she intensity change of at least one light among the lights intensity-modulated with she plurality of modulation frequency bands and the phase at which each of the plurality of images are captured may be output to the image processing unit 40.

In the image processing unit 40, the imaging information acquiring section 280 acquires the plurality of images captured, at different times, of the subject irradiated with lights intensity-modulated with a plurality of modulation frequency bands. The imaging information acquiring section 280 also acquires information indicating the phase differences between die phase of the intensity change of at least one light among the lights intensity-modulated with the plurality of modulation frequency bands and the phase at which each of the plurality of the images is captured. By demodulating the pixel values of the plurality of images acquired by the imaging information acquiring section 280, for each pixel, with the plurality of demodulation frequency bands or the plurality of demodulation frequencies based on the plurality of modulation frequency bands, the demodulating section 200 generates, for each pixel, a plurality of pieces of pixel information indicating amounts of subject light from the subject caused by each of the lights intensity-modulated by the plurality of modulation frequency bands. For example, the demodulating section 200 performs demodulation for each pixel using the plurality of modulation frequency bands as the demodulation frequency bands, for the pixel values of the plurality of images acquired by the imaging information acquiring section 280.

In the change frequency specifying section 240, the frequency of the change over time of the subject is specified by performing a frequency analysis on the pixel information obtained by having the demodulating section 200 perform demodulation with at least one modulation frequency band among the plurality of modulation frequency bands. The demodulating section 200 further generates the pixel information representing the change over time of the subject by demodulating the pixel values of the plurality of images using a frequency that is at least one of the difference between and the sum of at least one modulation frequency band among the plurality of modulation frequency bands and the frequency of the change over time of the subject.

The imaging system 5 described above images the subject using light that is reflected or scattered by the subject. However, the light used for the imaging is not limited to reflected or scattered light. For example, the imaging system 5 may image the subject using luminescent light generated from fee subject clue to the excitation of a luminescent substance included in the subject. In this case, the excitation light that excites this luminescent substance may be included as component light in the light from the light emitting section 130. For example, the IR light emitted by the light source 134 may be the excitation light that excites the luminescent material, and the imaging section 12 may image the subject with the subject light including the luminescent light generated as a result of the luminescent material being excited by the IR light. In this case, a wavelength filter that substantially blocks light in the IR light wavelength region emitted by the light source 134 and passes light in the luminescent light wavelength region may be provided on the subject-side surface of the imaging section 12. The luminescent material may be injected into the subject or applied to a surface of the subject. The luminescent substance may be an innate luminescent substance included in the subject. The luminescent light has a scope including fluorescent light, phosphorescent light, and the like.

An imaging system having a configuration similar to that of the imaging system 5 can be adopted as an endoscopic imaging system, in addition to she laparoscopic imaging system described above. An imaging system having a configuration similar to that of the imaging system 5 can be adopted as various other imaging systems. The imaging system 5 can be adopted as an imaging system for narrow spaces of dark spaces. An imaging system having a configuration similar to that of the imaging system 5 can be adopted as an imaging system for inside pipes or an imaging system for imaging relatively fine structures of the subject. The subject is not limited to a living organism, and may be various objects such as industrial products or the like.

The imaging system 5 described above multiplexes a plurality of lights intensity-modulated with different modulation frequencies and irradiates the subject, but can instead multiplex a plurality of lights intensity-modulated with different phases and irradiate the subject. In this case, the light emitting section 130 multiplexes a plurality of lights that are intensity-modulated with the same modulation frequency, have the same wavelength regions, and have different phases, and performs irradiation. As an example, the plurality of lights have phases differing from each other by 90° and, in the case of a single frequency signal, have a sine wave and cosine wave relationship. The subject light resulting from the light radiated by the imaging section 12 is then received and the imaging information acquiring section 280 acquires the imaging information data via the imaging information output section 150. The demodulating section 20 demodulates the pixel values of the plurality of images, for each pixel, using the phase information of each of the plurality of radiated lights. Specifically, by multiplying each of the pixel values of the plurality of images by a sine wave and a cosine wave, the demodulating section 200 separates the light into a subject light amount from the subject caused by the light whose intensity modulation phase is a sine wave and a subject light amount from the subject caused by the light whose intensity modulation phase is a cosine wave. In other words, the demodulating section 200 generates a plurality of pieces of pixel information indicating the subject light amount from the subject caused by each of the plurality of lights, for each pixel.

In the above description, at least a portion of fee process described as the operation of the image processing unit 40 can be realized by a processor controlling each piece of hardware, such as a hard disk and a memory, of a computer according to a program. In this way, at least a portion of the process of the image processing unit 40 can be realized by cooperation between a program and each piece of hardware including a processor, a hard disk, a memory, and the like, by having the processor operate according to the program to control each piece of hardware. In other words, the processes of each portion of the image processing unit 40, e.g. the processes of the imaging information acquiring section 280, the processes of the demodulating section 200, the processes of the change frequency specifying section 240, and the processes of the image generating section 220 can be realized through execution by a so-called computer. The computer may read the program, for controlling the execution of the processes described above, and operate according to she read program to execute these processes. The computer can read this program from a computer-readable storage medium that stores this program. Furthermore, tins program may be supplied to the computer through a communication line, and the computer may read the program supplied through the communication line.

Various embodiments of the present invention have been described with reference to processings and block diagrams whose blocks may represent (1) steps of processings in which operations are performed or (2) sections of apparatuses responsible for performing operations. Certain steps and sections may be implemented by dedicated circuitry, programmable circuitry supplies with computer-readable instructions stored on computer-readable media, and/or processors supplied with computer-readable instructions stored on computer-readable media. Dedicated circuitry may include digital and/or analog hardware circuits and may include integrated circuits (IC) and/or discrete circuits. Programmable circuitry may include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), etc. Processor may include electronic circuitry that implements the steps and/or sections according to stored instructions.

Computer-readable media may include any tangible device that can store instructions for execution by a suitable device, such that the computer-readable medium having instructions stored therein comprises an article of manufacture including instructions which can be executed to create means for performing operations specified in the processes or block diagrams. Examples of computer-readable media may include an electronic storage medium, a magnetic storage medium, an optical storage medium, an electromagnetic storage medium, a semiconductor storage medium, etc. More specific examples of computer-readable media may include a floppy disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a BLU-RAY(RTM) disc, a memory stick, an integrated circuit card, etc.

Computer-readable instructions may include assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, JAVA, C++, etc., and conventional procedural programming languages, such as the "C" programming language or similar programming languages.

Computer-readable instructions may be provided to a processor of a general purpose computer, special purpose computer, or other programmable data processing apparatus, or to programmable circuitry, locally or via a local area network (LAN), wide area network (WAN) such as the Internet, etc., to execute the computer-readable instructions to create means for performing operations specified in the processings or block diagrams. Examples of processors include computer processors, processing units, microprocessors, digital signal processors, controllers, microcontrollers, etc.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

LIST OF REFERENCE NUMERALS

5: imaging system, 10: imaging element, 12: imaging section, 14: objective lens, f1: modulation frequency, f2 modulation frequency, f3 modulation frequency, f4: modulation frequency, 20: scope section, 22: light guide, 24: light emission opening, 26: light input opening, 30: control unit, 40: image processing unit, 50: display apparatus, 60: storage apparatus, 70: output apparatus, 100: imaging element, 101: microlens, 103: passivation film, 104: photodiode 105: transistor, 106: photodiode layer, 107: wiring, 108: wiring layer, 109: bump, 110; silicon penetration electrode, 111: signal processing chip, 112: memory chip, 313; imaging chip, 120: imaging control section, 130: light emitting section, 131: light source, 132; light source, 133; light source, 134: light source, 140: light emission control section, 150: imaging information output section, 200: demodulating section, 220: image generating section, 240: change frequency specifying section, 250: selecting section, 260: storage apparatus, 280: imaging information acquiring section, 301: pixel, 320: image, 330: image, 340: image, 381: sequence, 382: sequence, 383: sequence, 384: sequence, 390: sequence, 392: sequence, 400: image group, 410; image, 420: image, 430: image, 440: image, 530: multiplication, 512: frequency filter, 520; multiplication, 522; frequency filter, 530: multiplication, 532: frequency fiber, 540; multiplication, 542: frequency filter, 710, 720, 730, 740: image

What is claimed is:

1. An image processing apparatus comprising:
   an image acquiring section that acquires a plurality of images obtained by imaging, at different times, a subject irradiated with lights intensity-modulated with a plurality of modulation frequencies or modulation frequency bands; and
   a demodulating section that demodulate pixel value of the plurality of images with a plurality of demodulation frequencies or demodulation frequency bands based on the plurality of modulation frequencies or modulation frequency bands, for each pixel, thereby generating a plurality of pieces of pixel information indicating subject light amounts from the subject caused by each of the lights intensity-modulated with the plurality of modulation frequencies or modulation frequency bands, for each pixel.

2. The image processing apparatus according to claim 1, wherein
   the demodulating section demodulates the pixel values of the plurality of images using the plurality of modulation frequencies or modulation frequency bands as the demodulation frequencies or demodulation frequency bands, for each pixel.

3. The image processing apparatus according to claim 1, further comprising:
   a change frequency specifying section that specifies a frequency of change over time of the subject by performing a frequency analysis on pixel information obtained by having the demodulating section perform demodulation with at least one modulation frequency or modulation frequency band, from among the plurality of modulation frequencies or modulation frequency bands, wherein
   the demodulating section further generates pixel information representing the change over time of the subject, by demodulating the pixel values of the plurality of images using a frequency that is at least one of a sum of or a difference between at least one modulation frequency among the plurality of modulation frequencies or modulation frequency bands and the frequency of the change over time of the subject.

4. The image processing apparatus according to claim 1, further comprising:
   a phase difference information acquiring section that acquires information indicating phase differences between a phase of an intensity change of at least one light among the lights intensity-modulated with the plurality of modulation frequencies or modulation frequency bands and a phase at which each of the plurality of images is captured.

5. The image processing apparatus according to claim 1, wherein
   the image acquiring section acquires the plurality of images obtained by imaging the subject that is irradiated by lights having a plurality of wavelength regions and intensity-modulated with the plurality of modulation frequencies or modulation frequency bands.

6. The image processing apparatus according to claim 5, wherein
   the plurality of wavelength regions include a first color component wavelength region associated with a visible region, a second color component wavelength region associated with a visible region, and a third color component wavelength region associated with a visible region, the plurality of images are images of the subject irradiated by light of the first color component wavelength region intensity-modulated with a first modulation frequency or modulation frequency band, light of the second color component wavelength region intensity-modulated with a second modulation frequency or modulation frequency band, and light of the third color component wavelength region intensity-modulated with a third modulation frequency or modulation frequency band, and the demodulating section demodulates the pixel value of the plurality of images with a first demodulation frequency or demodulation frequency baud, for each pixel, thereby generating pixel information of the first color component for each pixel; demodulates the pixel values of the plurality of images with a second demodulation frequency or demodulation frequency band, for each pixel, thereby generating pixel information of the second color component for each pixel; and demodulates the pixel values of the plurality of images with a third demodulation frequency or demodulation frequency band, for each pixel, thereby generating pixel information of the third color component for each pixel.

7. The image processing apparatus according to claim 1, wherein
the image acquiring section acquires a plurality of images obtained by imaging the subject that is irradiated by lights that have matching wavelength regions and are intensity-modulated with the plurality of modulation frequencies or modulation frequency bands.

8. The image processing apparatus according to claim 1, wherein
the demodulating section demodulates the pixel values of the plurality of images with the plurality of demodulation frequencies or demodulation frequency bands, for each pixel, thereby generating the plurality of pieces of pixel information for each pixel, and
the imaging processing apparatus further comprises an image generating section that generates images caused by light from the subject due to each of the lights intensity-modulated with the plurality of modulation frequencies, based on the plurality of pieces of pixel information of each pixel generated by the demodulating section.

9. The image processing apparatus according to claim 1, further comprising:
a selecting section that selects one of the plurality of demodulation frequencies and demodulation frequency bands, wherein
the demodulating section performs demodulation with the selected demodulation frequency or demodulation frequency band.

10. The image processing apparatus according to claim 9, wherein
the selecting section selects, from among the plurality of demodulation frequencies and demodulation frequency bands, a demodulation frequency or demodulation frequency band with a greatest difference relative to a frequency of a time change of background light.

11. The image processing apparatus according to claim 9, wherein
the selecting section selects, from among the plurality of demodulation frequencies, a demodulation frequency that is n times (n is an integer) a frequency of a time change of background light.

12. The image processing apparatus according to claim 11, wherein
the selecting section selects, from among the plurality of demodulation frequencies, a demodulation frequency that is $2^n$ times (n is an integer) the frequency of the time change of the background light.

13. The image processing apparatus according to claim 1, wherein
the image acquiring section acquires a plurality of images captured with a frequency higher than any one of the plurality of modulation frequencies and modulation frequency bands.

14. The image processing apparatus according to claim 1, wherein
the image acquiring section acquires images captured a plurality of times with different phases and with a frequency lower than any one of at least the plurality of modulation frequencies or modulation frequency bands.

15. The image processing apparatus according to claim 1, wherein
the plurality of modulation frequencies have a relationship of being n times (n is an integer) each other.

16. The image processing apparatus according to claim 1, wherein
the plurality of modulation frequencies have a relationship of being $2^n$ times (n is an integer) each other.

17. An imaging apparatus comprising:
the image processing apparatus according to claim 1; and
an image sensor that captures the plurality of images.

18. The imaging apparatus according to claim 17, further comprising:
a light source that emits the lights intensity-modulated with the plurality of modulation frequencies or modulation frequency bands.

19. The imaging apparatus according to claim 17, further comprising;
an imaging chip that includes the image sensor; and
a signal processing chip that includes a processing circuit for processing a pixel signal output from the image sensor, wherein
the imaging chip and the signal processing chip are electrically connected with a layered structure.

20. The imaging apparatus according to claim 17, further comprising:
an imaging control section that causes the imaging section to capture each of the plurality of images in synchronization with an intensity change of light modulated with at least one modulation frequency or modulation frequency band from among the plurality of modulation frequencies and modulation frequency bands.

21. An image processing apparatus comprising:
an image acquiring section, that acquires a plurality of images obtained by imaging, at different times, a subject irradiated by multiplexing a plurality of lights that are intensity-modulated and have different phases from each other; and
a demodulating section that demodulates pixel values of the plurality of images using phase information of each of the plurality of lights, for each pixel, thereby generating a plurality of pieces of pixel information indicating subject light amounts from foe subject caused by each of the plurality of lights, for each pixel.

22. An imaging apparatus comprising:
the image processing apparatus according to claim 21;
a light source that emits the plurality of lights; and
an image sensor that captures the plurality of images.

23. An imaging apparatus comprising:
a light source that emits lights intensity-modulated with a plurality of modulation frequencies or modulation frequency bands;
an image sensor that images a subject irradiated by the lights; and
an output section that outputs a plurality of images of the subject captured at different times by the image sensor, in association with information indicating the plurality of modulation frequencies or modulation frequency bands, to an image processing apparatus that, for each pixel, performs demodulation with a plurality of demodulation frequencies or demodulation frequency bands based on the plurality of modulation frequencies or modulation frequency bands.

24. The imaging apparatus according to claim 23, wherein the output section further outputs, in association with the plurality of images, information indicating phase differences between a phase of an intensity change of at least one light among the lights intensity-modulated with the plurality of modulation frequencies or modulation frequency bands and a phase at which each of the plurality of images is captured.

25. A machine-readable medium storing thereon a program that causes a computer to:
acquire a plurality of images obtained by imaging a subject irradiated with lights intensity-modulated with a plurality of modulation frequencies or modulation frequency bands differing from each other; and
demodulate pixel values of the plurality of images with a plurality of demodulation frequencies or demodulation frequency bands based on the plurality of modulation frequencies or modulation frequency bands, for each pixel, thereby generating a plurality of pieces of pixel information indicating subject light amounts from the subject caused by each of the lights intensity-modulated with the plurality of modulation frequencies or modulation frequency bands, for each pixel.

26. An image processing apparatus comprising:
a processor configured to perform operations including:
acquiring a plurality of images obtained by imaging, at different times, a subject irradiated with lights intensity-modulated with a plurality of modulation frequencies or modulation frequency bands; and
demodulating pixel values of the plurality of images with a plurality of demodulation frequencies or demodulation frequency bands based on the plurality of modulation frequencies or modulation frequency bands, for each pixel, thereby generating a plurality of pieces of pixel information indicating subject light amounts from the subject caused by each of the lights intensity-modulated with the plurality of modulation frequencies or modulation frequency bands, for each pixel.

27. An image processing apparatus comprising:
a processor configured to perform operations including:
acquiring a plurality of images obtained by imaging, at different times, a subject irradiated by multiplexing a plurality of lights that are intensity-modulated and have different phases from each other; and
demodulating pixel values of the plurality of images using phase information of each of the plurality of lights, for each pixel, thereby generating a plurality of pieces of pixel information indicating subject light amounts from the subject caused by each of the plurality of lights, for each pixel.

28. An imaging apparatus comprising:
a light source that emits lights intensity-modulated with a plurality of modulation frequencies or modulation frequency bands;
an image sensor that images a subject irradiated by the lights; and
a processor configured to perioral operations including:
outputting a plurality of images of the subject captured at different times by the image sensor, in association with information indicating the plurality of modulation frequencies or modulation frequency bands, to an image processing apparatus that, for each pixel, performs demodulation with a plurality of demodulation frequencies or demodulation frequency bands based on the plurality of modulation frequencies or modulation frequency bands.

* * * * *